(12) United States Patent
Shull et al.

(10) Patent No.: US 12,333,073 B2
(45) Date of Patent: Jun. 17, 2025

(54) SYSTEMS AND METHODS FOR MULTIPLEXED AMPLIFIERS FOR BRAIN COMPUTER INTERFACES

(71) Applicants: Duke University, Durham, NC (US); The Trustees of Dartmouth College, Hanover, NH (US)

(72) Inventors: Gabriella Shull, Durham, NC (US); Jonathan Viventi, Durham, NC (US); Thomas Jochum, Durham, NC (US); Hui Fang, Hanover, NH (US); Michael Trumpis, Berkeley, CA (US)

(73) Assignees: Duke University, Durham, NC (US); The Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 18/486,735

(22) Filed: Oct. 13, 2023

(65) Prior Publication Data
US 2024/0134452 A1   Apr. 25, 2024

Related U.S. Application Data

(60) Provisional application No. 63/415,758, filed on Oct. 13, 2022.

(51) Int. Cl.
*A61B 5/00* (2006.01)
*A61B 5/05* (2021.01)
*G06F 3/01* (2006.01)

(52) U.S. Cl.
CPC ........ *G06F 3/015* (2013.01); *G06F 2203/011* (2013.01)

(58) Field of Classification Search
CPC ......... A61B 5/369; A61B 5/291; A61B 5/372; A61B 5/30; A61B 5/0006; A61B 5/24;
(Continued)

(56) References Cited

U.S. PATENT DOCUMENTS

2008/0015459 A1   1/2008  Llinas
2011/0054583 A1*  3/2011  Litt .................. A61B 5/291
                                                    600/377
(Continued)

OTHER PUBLICATIONS

Akam et al. "Oscillatory multiplexing of population codes for selective communication in the mammalian brain" Nat Rev Neurosci. Feb. 2014; 15(2): 111-122. (Year: 2014).*
(Continued)

*Primary Examiner* — Joseph A Stoklosa
*Assistant Examiner* — Brian M Antiskay
(74) *Attorney, Agent, or Firm* — Armstrong Teasdale LLP

(57) ABSTRACT

A brain computer interface for interfacing with a brain of a subject is provided. The brain computer interface includes one or more shanks. Each shank includes an array of pixels and output traces. Each pixel includes an electrode and a front-end circuit positioned at a site of the electrode. The front-end circuit is configured to reduce noise in signals recorded by the electrode, and further configured to multiplex the signals. A density of power consumption of the each pixel is equal to or less than 1 µW per area of 50 µm by 50 µm. The output traces are electrically coupled with the array of pixels. A number of output traces is less than a number of pixels in the array due to multiplexing. The one or more shanks are configured to be inserted on and/or into a brain of a subject.

21 Claims, 29 Drawing Sheets

(58) Field of Classification Search
CPC ... A61B 5/6814; A61B 5/7203; A61B 5/7225; A61B 5/31; A61B 5/384; A61B 5/0031; A61B 5/165
USPC .............. 600/372–373, 377–378, 544–545
See application file for complete search history.

(56) References Cited

U.S. PATENT DOCUMENTS

| | | | | |
|---|---|---|---|---|
| 2014/0330102 | A1* | 11/2014 | Zbrzeski | A61B 5/7225 600/377 |
| 2016/0278713 | A1* | 9/2016 | Shoaran | A61B 5/7232 |
| 2017/0347888 | A1 | 12/2017 | Roukes | |
| 2019/0000377 | A1* | 1/2019 | Lei | A61B 5/4836 |
| 2020/0155828 | A1* | 5/2020 | Shepard | A61B 5/293 |
| 2021/0308468 | A1 | 10/2021 | Shepard | |
| 2021/0361180 | A1* | 11/2021 | Chien | A61B 5/02427 |
| 2022/0240846 | A1 | 8/2022 | Howard | |

OTHER PUBLICATIONS

Trumpis et al. "Sufficient sampling for kriging prediction of cortical potential in rat, monkey, and human µECoG" J. Neural Eng. 18 (2021). Mar. 2021 (Year: 2021).*

Aziz et al. "256-Channel Integrated Neural Interface and Spatio-Temporal Signal Processor" Conference Paper. Jun. 2006. (Year: 2006).*

Sahasrabuddhe, et al, "The Argo: a high channel count recording system for neural recording in vivo", Journal of Neural Engineering, vol. 18, No. 1, Feb. 5, 2021, pp. 1-18. DOI: 10.1088/1741-2552/abd0ce.

Angotzi, et al, "SiNAPS: An implantable active pixel sensor CMOS-probe for simultaneous large-scale neural recordings", Biosensors and Bioelectronics, vol. 126, Feb. 1, 2019, pp. 355-164. DOI: 10.1016/j.bios.2018.10.032.

Steinmetz et al. "Neuropixels 2.0: A miniaturized high-density probe for stable, long-term brain recordings", Science, vol. 372, Issue 6539, Apr. 16, 2021, pp. 1-10. DOI:10.1126/science.abf4588.

Insanally, et al, "A low-cost, multiplexed µECoG system for high-density recordings in freely moving rodents", Journal of Neural Engineering, vol. 13, No. 2, Mar. 15, 2016, pp. 1-13. DOI: 10.1088/1741-2560/13/2/026030.

Rivnay et al., "Next-generation probes, particles, and proteins for neural interfacing", Science Advances, vol. 3, Issue 8, Jun. 9, 2017, pp. 1-20. DOI:10.1126/sciadv.1601649.

Chang, et al., "Materials and processing approaches for foundry-compatible transient electronics", PNAS, vol. 114, No. 28, Jun. 26, 2017, pp. E5522-E5529. DOI: 10.1073/pnas.1707849114.

Tsai, et al., "A very large-scale microelectrode array for cellular-resolution electrophysiology", Nature Communications, vol. 8, Article 1802, Nov. 27, 2017, pp. 1-11. DOI: 10.1038/s41467-017-02009-x.

Fang, et al., "Capacitively coupled arrays of multiplexed flexible silicon transistors for long-term cardiac electrophysiology", Nature Biomedical Engineering, vol. 1, Article 38, pp. 1-12. DOI: 10.1038/s41551-017-0038.

"BioNinja", Retrieved from Internet: https://ib.bioninja.com.au/options/option-a-neurobiology-and/a2-the-human-brain/sensorimotor-areas.html.

Benabid, et al., "An exoskeleton controlled by an epidural wireless brain-machine interface in a tetraplegic patient: a proof-of-concept demonstration", The Lancet Neurology, vol. 18, Issue 12, Oct. 3, 2019, pp. P1112-P1122. DOI: 10.1016/S1474-4422(19)30321-7.

Chiang et al., "Development of a neural interface for high-definition, long-term recording in rodents and nonhuman primates", Science Translational Medicine, vol. 12, Issue 538, Apr. 8, 2020, pp. 1-12. DOI: 10.1126/scitranslmed.aay4682.

Song, et al., "Flexible electronic/optoelectronic microsystems with scalable designs for chronic biointegration", PNAS, vol. 116, No. 31, Jul. 15, 2019, pp. 15398-15406. DOI: 10.1073/pnas.1907697116.

Polley et al., "Multiparametric Auditory Receptive Field Organization across Five Cortical Fields in the Albino Rat", Journal of Neurophysiology, vol. 97, Mar. 21, 2007, pp. 3621-3638. DOI: 10.1152/jn.01298.2006.

Woods et al., "Long-term recording reliability of liquid crystal polymer µECoG arrays", Journal of Neural Engineering, vol. 15, 2018, pp. 1-36.

Kolodziej et al., "Matlab FE_Toolbox—an universal utility for feature extraction of EEG signals for BCI realization", Electrical Review, 2010, pp. 44-46, ISSN 0033-2097.

A. J. Williams, M. Trumpis, B. Bent, C. -H. Chiang and J. Viventi, "A Novel µECoG Electrode Interface for Comparison of Local and Common Averaged Referenced Signals," 2018 40th Annual International Conference of the IEEE Engineering in Medicine and Biology Society (EMBC), Honolulu, HI, USA, 2018, pp. 5057-5060, doi: 10.1109/EMBC.2018.8513432.

Duraivel, S., Rahimpour, S., Chiang, CH. et al. High-resolution neural recordings improve the accuracy of speech decoding. Nat Commun 14, 6938 (2023). https://doi.org/10.1038/s41467-023-42555-1.

Froemke, R., Merzenich, M. & Schreiner, C. A synaptic memory trace for cortical receptive field plasticity. Nature 450, 425-429 (2007). https://doi.org/10.1038/nature06289.

Viventi, J., Kim, DH., Vigeland, L. et al. Flexible, foldable, actively multiplexed, high-density electrode array for mapping brain activity in vivo. Nat Neurosci 14, 1599-1605 (2011). https://doi.org/10.1038/nn.2973.

Sharma, M.; Gardner, A.T.; Strathman, H.J.; Warren, D.J.; Silver, J.; Walker, R.M. Acquisition of Neural Action Potentials Using Rapid Multiplexing Directly at the Electrodes. Micromachines 2018, 9, 477. https://doi.org/10.3390/mi9100477.

D. M. Brandman, S. S. Cash and L. R. Hochberg, "Review: Human Intracortical Recording and Neural Decoding for Brain-Computer Interfaces," in IEEE Transactions on Neural Systems and Rehabilitation Engineering, vol. 25, No. 10, pp. 1687-1696, Oct. 2017, doi: 10.1109/TNSRE.2017.2677443.

Hochberg, L., Serruya, M., Friehs, G. et al. Neuronal ensemble control of prosthetic devices by a human with tetraplegia. Nature 442, 164-171 (2006). https://doi.org/10.1038/nature04970.

McLeish, J. and Haeberle, R., "Moving Automotive Electronics from Reliability/Durability Testing to Virtual Validation Modeling Using a Physics of Failure CAE App," SAE Int. J. Passeng. Cars—Electron. Electr. Syst. 7(2):369-376, 2014, https://doi.org/10.4271/2014-01-0233.

Razavi, Behzad. Design of analog CMOS integrated circuits. Tata McGraw-Hill Education, 2002.

"Speech synthesis from neural decoding of spoken sentences", USCF Neurosurgery, Retrieved from Internet: https://www.youtube.com/watch?v=kbX9FLJ6WKw.

T. M. Seese, H. Harasaki, G. M. Saidel, and C. R. Davies, "Characterization of tissue morphology, angiogenesis, and temperature in the adaptive response of muscle tissue to chronic heating," Lab. Investig., vol. 78, No. 12, pp. 1553-1562, Dec. 1998.

P. D. Wolf, "Thermal Considerations for the Design of an Implanted Cortical Brain-Machine Interface (BMI)," Indwelling Neural Implant. Strateg. Contend. with Vivo Environ., pp. 63-86, Jan. 2008, doi: 10.1201/9781420009309.ch3.

C. H. Chiang et al., "A modular high-density µeCoG system on macaque vlPFC for auditory cognitive decoding," J. Neural Eng., vol. 17, No. 4, p. 046008, Aug. 2020, doi: 10.1088/1741-2552/ab9986.

Vetreno RP, Yaxley R, Paniagua B, Johnson GA, Crews FT. Adult rat cortical thickness changes across age and following adolescent intermittent ethanol treatment. Addict Biol. May 2017;22(3):712-723. doi: 10.1111/adb.12364.

Mengler L, Khmelinskii A, Diedenhofen M, Po C, Staring M, Lelieveldt BP, Hoehn M. Brain maturation of the adolescent rat cortex and striatum: changes in volume and myelination. Neuroimage. Jan. 1, 2014;84:35-44. doi: 10.1016/j.neuroimage.2013.08.034.

"An Introduction to Probe Cards", Denis Place, published Nov. 21, 207, Retrieved from Internet: https://blog.semiprobe.com/probe-card.

(56) References Cited

OTHER PUBLICATIONS

"Aspect L1", Retrieved from Internet: https://www.wentworthlabs.com/manual-analytical-prober-aspect-11/.
Morshed et al., "BSIM4v4.7 MOSFET Model", Department of Electrical Engineering and Computer Sciences University of California, published 2011.
Kolodziej, Andrzej M., et al. "A new method of feature extraction from EEG signal for brain-computer interface design" Warsaw University of Technology, Institute of the Theory of Electrical Engineering, Measurement and Information Systems, 4 pps.
"Xfab" Retrieved from the Internet: https://www.xfab.com/.
"Paradromics" Retrieved from the Internet: https://www.paradromics.com/.
"Neuropixels" Retrieved from the Internet: https://www.neuropixels.org/.
"Plexon" Retrieved from the Internet: https://plexon.com/products/sinaps/.
Fitzgerald, M.J., et al, (2012) Clincal neuroanatomy and neuroscience, 6th edition pp. 300-303.
International Search Report and Written Opinion for PCT Application No. PCT/US2023/076826 mailed Mar. 25, 2024; 14 pp.

\* cited by examiner

| Spec | Target |
|---|---|
| -3dB HPF | 0.1 Hz |
| -3dB LPF | 10 kHz |
| Input Referred Noise (1 - 10 kHz) | <10 μV |
| Input Referred Noise (10 - 10 kHz) | <10 μV |
| Input Referred Noise (300 - 10 kHz) | <10 μV |
| Gain | Set by Noise |
| Area | ≤ 50 μm x 50 μm |
| Power Consumption/channel | <1 μW |

| | Neuropixel | SiNaps 502-s | Paradromics 502-p | BrainComputer Interface 102 |
|---|---|---|---|---|
| Recording Bandwidth | 0.5 Hz - 10 kHz | 300 - 10 kHz | 18 Hz - 10 kHz | 0.05 Hz - 10 kHz |
| Noise (300 Hz - 10 kHz) | 8.2 μV | 7.5 μV | 6.3 μV* | 8.35 μV |
| Multiplexed during recording? | No | yes | yes | yes |
| Multiplexing ratio | - | 32:1 | 64:1 | 32:1 |
| Simultaneously Recorded Channels | 384 | 512 | 30,000 | 384 |
| Sampling Rate per Channel | 30 kHz | 25 kHz | 32 kHz | 30 kHz |
| Power Consumption per Channel | N/A | 6 μW | N/A | 0.63 μW |
| Supply Voltage | 5V | 1.8V | 5V | 1.2V |

* Indicates noise in 300 Hz - 6 kHz band.

FIG. 5B

| Specification | Neuropixels | Neuro-CROWN (this work) |
|---|---|---|
| Channels | 384 | 2,048 |
| On-site multiplexing | NO | YES |
| Noise | 9 µV rms | 1.7 fC rms |
| SNR* | 38 dB | >48 dB |
| Noise bandwidth | 0.5 - 1000 Hz | 1 - 390 Hz |
| Electrode pitch | 25 µm | 50 µm |
| Form factor | 1D, rigid | 3D, flexible |

FIG. 14

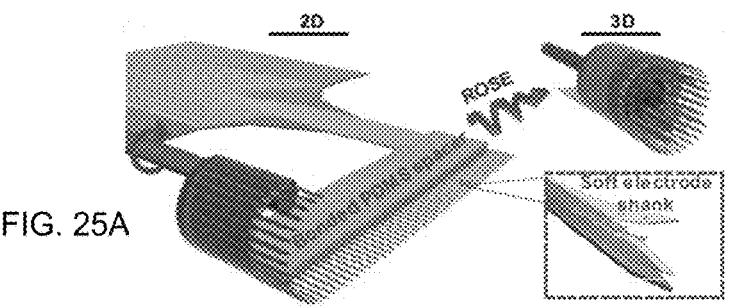
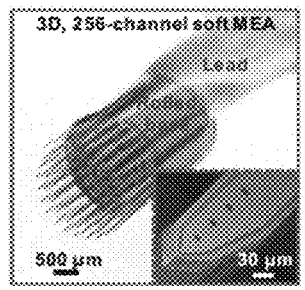
FIG. 25A
FIG. 25B
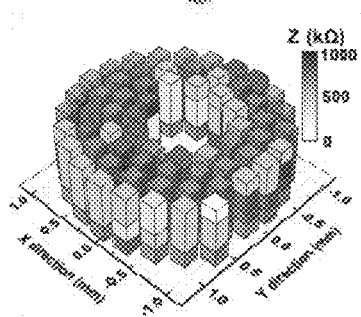
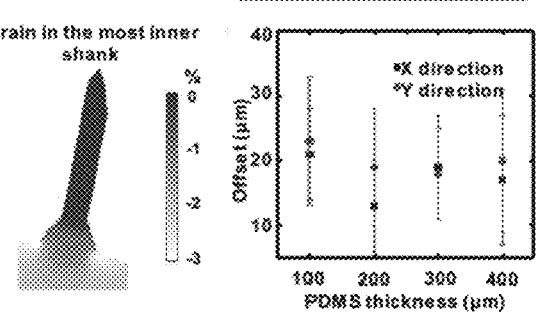
FIG. 25C
FIG. 25D
FIG. 25E ID # SYSTEMS AND METHODS FOR MULTIPLEXED AMPLIFIERS FOR BRAIN COMPUTER INTERFACES

CROSS-REFERENCE TO RELATED APPLICATION

This patent application claims the benefit of U.S. Provisional Patent Application No. 63/415,758, filed on Oct. 13, 2022, titled "SYSTEMS AND METHODS FOR MULTIPLEXED AMPLIFIERS FOR NEURAL INTERFACING AT ELECTRODE SITE," the entire contents and disclosures of which are hereby incorporated herein by reference in their entirety.

STATEMENT REGARDING FEDERALLY SPONSORED RESEARCH & DEVELOPMENT

This invention was made with government support under Federal Grant No. 1U01NS123668-01 awarded by the National Institutes of Health National Institute of Neurological Disorder & Stroke and by Federal Grant No. DGE-1644868 awarded by the National Science Foundation. The government has certain rights in the invention.

BACKGROUND

The field of the disclosure relates generally to systems and methods of neural interfaces, and more particularly, to systems and methods for brain computer interfaces.

Brain computer interfaces (BCI) are used to restore or supplement at least part of brain functions that were degraded or lost due to injury or diseases. Brain signals are detected by a brain computer interface and processed to generate commands for BCI applications to perform functions such as generating speech based on the brain signals. Known brain computer interfaces and systems and methods for them are disadvantaged in some aspects and improvements are desired.

BRIEF DESCRIPTION

In one aspect, a brain computer interface for interfacing with a brain of a subject is provided. The brain computer interface includes one or more shanks. Each shank includes an array of pixels and output traces. Each pixel includes an electrode and a front-end circuit positioned at a site of the electrode. The front-end circuit is configured to reduce noise in signals recorded by the electrode, and further configured to multiplex the signals. A density of power consumption of the each pixel is equal to or less than 1 µW per area of 50 µm by 50 µm. The output traces are electrically coupled with the array of pixels. A number of output traces is less than a number of pixels in the array due to multiplexing. The one or more shanks are configured to be inserted on and/or into a brain of a subject.

In another aspect, a method of fabricating a brain computer interface for interfacing with a brain of a subject is provided. The method includes forming one or more shanks. Each shank includes an array of pixels and output traces. Each pixel includes an electrode, and a front-end circuit at a site of the electrode. The front-end circuit is configured to reduce noise in signals recorded by the electrode, and further configured to multiplex the signals. A density of power consumption of the each pixel is equal to or less than 1 µW per area of 50 µm by 50 µm. The output traces are electrically coupled with the array of pixels. A number of output traces is less than a number of pixels in the array due to multiplexing. The one or more shanks are configured to be inserted on and/or into a brain of a subject. The method also includes transferring the one or more shanks to a substrate.

In one more aspect, a brain computer interface system is provided. The brain computer interface system includes a brain computer interface configured to interface with neurons of a brain of a subject. The brain computer interface includes one or more shanks. Each shank includes an array of pixels and output traces. Each pixel includes an electrode, and a front-end circuit positioned at a site of the electrode. The front-end circuit is configured to reduce noise in signals recorded by the electrode, and further configured to multiplex the signals. A density of power consumption of the each pixel is equal to or less than 1 µW per area of 50 µm by 50 µm. The output traces are electrically coupled with the array of pixels, wherein a number of output traces is less than a number of pixels in the array due to multiplexing. The one or more shanks are configured to be inserted on and/or into a brain of a subject. The brain computer interface system further includes a brain computer interface (BCI) computing device electrically coupled with the brain computer interface. The BCI computing device includes at least one processor in communication with at least one memory device. The at least one processor is programmed to process signals output by the brain computer interface.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 5A is a performance matrix of an example brain computer interface.

FIG. 5B is a comparison of the performance of the example brain computer interface with that of known brain computer interfaces.

FIG. 14 provides a table of performance specifications. The signal to noise ratio (SNR) was measured in vitro using a 2 mVpp sine wave at 10 Hz for all devices. The Neuro-CROWN SNR was measured using prototype devices.

FIG. 15A shows that active electrodes use a 2T design with a source-follower amplifier (T1) and a multiplexing transistor (T2) to record multiplexed neural signals. FIG. 15B shows 1T multiplexed, current-sensing (CS) design for increased SNR. Neural currents from the electrode (Input) are integrated on a relatively small (10 pF) capacitor. A single transistor (T1) at each electrode is periodically switched on to measure and reset the integrated charge on the capacitor using an external, ultra-low noise, current-sensing amplifier.

FIG. 18A is an image of 1T CS electrode array placed on the surface of rodent primary auditory cortex. The inset in the middle shows annotations of the electrode positions in the array. The insets on the right show averaged responses from 3 independent electrodes. FIG. 18B shows single-trial neural responses to three successive tone stimuli from tone task described in task 1.2. FIG. 18C shows the active, multiplexed 1T CS array achieved higher decoding performance than a passive array.

FIG. 19A shows 61-ch µECoG passive array currently being disseminated to end-users. The electrodes are 200 µm in diameter with a pitch of 400 µm. FIG. 19B shows 4096-ch active µECoG array to be sent to end-users. The electrodes are 40×40 µm² with a pitch of 50 yielding a 64-fold increase in density compared to the current devices. The insets shows four electrodes and associated transistor circuits. These four electrodes fit in the space shown in the small orange square at left. Integrated multiplexing allows all 4,096 electrodes to be recorded simultaneously using only 18 external wire connections. The overall geometry of the arrays are identical, allowing end-users to easily upgrade experiments to single-cell resolution.

In FIG. 20A, the variance of signal differences (semivariance) as a function of electrode-electrode distance (squares) was fit with a Matern covariance function (the curves) parameterized by range (theta), and smoothness (nu). The kriging filter from this model, with a moderate 9.3% noise level, had an expected prediction error of 1.9% of the noiseless field power. In FIG. 20B, the filtering was adapted to a set of frames with rougher texture and higher noise. The expected filtering error was 5.9%.

In FIG. 22A, the mean square error (MSE) between the filtered and true frames improved with longer characteristic lengths indicated by covariance models. The model-based filtering error (shown as dashed lines per noise level) accurately predicted the real MSE. In FIG. 22B, median filtering efficiency per noise level is shown. Higher amounts of noise resulted in noisier filtered frames, but noise reduction ratio also increased.

In FIG. 24A, a STRF kernel of a single µECoG channel expresses the high-gamma response strength as a function of frequency and time. In FIG. 24B, the Pearson correlation between predicted and recorded high gamma power rose on average across channels following denoising (Mann-Whitney U, p<0.001).

FIGS. 25A-25G show rolling of 2D soft electrode array (ROSE) method. FIG. 25A is schematic illustration of the ROSE method. FIG. 25B shows a prototypical 256-ch 3D flexible MEA with 64 shanks from the ROSE method. FIG. 25C is 3D impedance heatmap of the array in FIG. 25B. FIG. 25D shows train distribution in the rolled base region of the array in FIG. 25B. FIG. 25E shows shank position offset from theoretical prediction as a function of the polydimethylsiloxane (PDMS) spacer layer thickness. FIG. 25F shows insertion force dynamics of the array in FIG. 25B inside agarose gel brain phantom. FIG. 25G shows in vivo validation of the 3D ROSE array in rat.

FIG. 26A shows deterministic transfer printing and interconnecting of ultra-thin (2.1 µm) CMOS chiplets. FIG. 26B shows schematic layout and dimensions of the 2D precursor array which, after ROSE, are converted to a 2,048-ch Neuro-CROWN. The depiction is drawn to scale. FIG. 26C shows partial stiffening strategy to insert all 64 shanks from Neuro-CROWN without increasing the insertion footprint.

Unless otherwise indicated, the drawings provided herein are meant to illustrate features of embodiments of the disclosure. These features are believed to be applicable in a wide variety of systems including one or more embodiments of the disclosure. As such, the drawings are not meant to include all conventional features known by those of ordinary skill in the art to be required for the practice of the embodiments disclosed herein.

DETAILED DESCRIPTION

This disclosure includes systems and methods for brain computer interface for interfacing with a brain of a subject. As used herein, a subject is a human, an animal, or a phantom, or part of a human, an animal, or a phantom, such as an organ or tissue. Method aspects will be in part apparent and in part explicitly discussed in the following description.

Figure 1A:
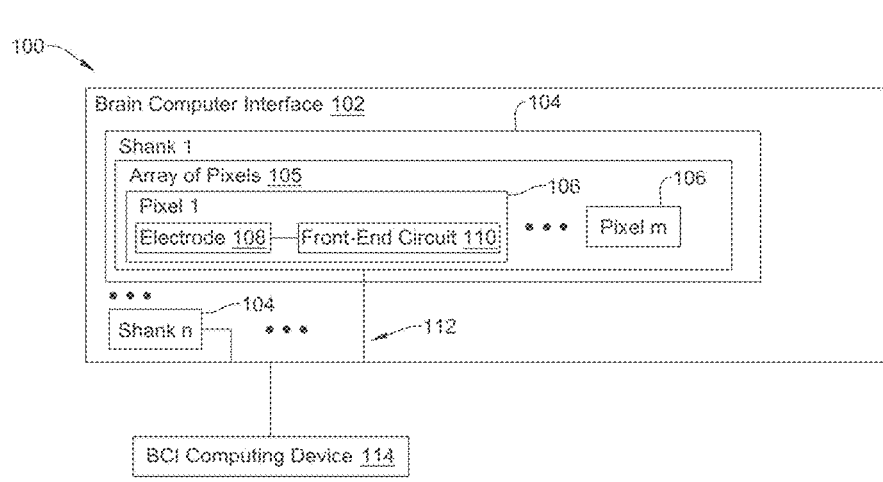
FIG. 1A is a schematic diagram of one suitable embodiment of a brain computer interface system.
Figure 1B:
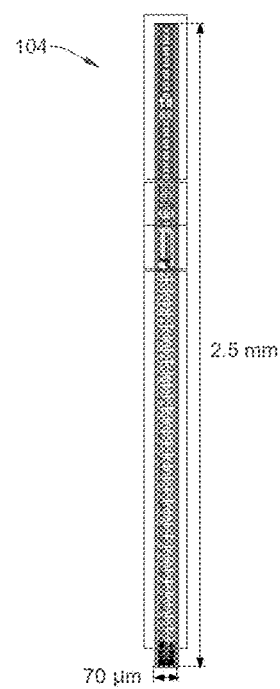
FIG. 1B shows a shank of one suitable embodiment.

FIG. 1A is a schematic diagram of a brain computer interface (BCI) system 100. In the example embodiment, the brain computer interface system 100 includes a brain computer interface 102 configured to interface with neurons of a brain of a subject. The brain computer interface 102 includes shanks 104. A shank 104 includes an array 105 of pixels 106. FIG. 1B is a schematic diagram of an example shank 104. In the example, in a surface area of 2.5 mm by 70 μm, the shank 104 includes an array 105 of pixels 106 in a 32-by-1 array. A pixel may also be referred to as a channel. Each pixel 106 includes an electrode 108. In the example, the pitch in the shank 104, or the distance between the center of an electrode 108 and the center of its immediately neighboring electrode 108, is 50 μm. The pixel 106 also includes a front-end circuit 110. The front-end circuit 110 is configured to reduce noise in the signals and multiplex signals recorded from the electrodes. The shank 104 also includes output traces 112 electrically coupled with the array 105 of pixels. The number of output traces 112 is reduced from the number of pixels 106 in the array due to multiplexing. The front-end circuit 110 is positioned at the site of electrode 108, where signals recorded from an electrode 108 are directly passed on to the front-end circuit 110, without an output trace 112 between the electrode 108 and the front-end circuit 110. The density of power consumption of the shanks 104 is equal to or less than 1 μW per area of 50 μm by 50 μm such that the power consumption at shanks 104 does not incur any damage to neurons.

In the example embodiment, the brain computer interface system 100 further includes a BCI computing device 114. The BCI computing device 114 is electrically coupled with the brain computer interface 102 via output traces 112, where brain signals detected by electrodes 108 are transmitted to BCI computing device via output traces 112. The brain signals are further processed by the BCI computing device 114. For example, kriging may be applied to further reduce noise in local field potentials in the brain signals. The brain signals may be further processed such as performing feature extraction and classification. The processed signals are used to generate commands to be input into an BCI application that perform functions directed by brain signals, such as generating synthesized speech based on the brain signals.

Signals recorded from neurons includes components of local field potentials at a relatively low frequency range such as a frequency less than 250 Hz, and components of action potentials at a relatively high frequency range such as in the range from approximately 250 Hz to 10 kHz. The frequency range of the brain computer interface system 100 may span from 0.05 Hz to 10 kHz, thereby sampling the entire spectrum of neural responses, unlike some known brain computer interface systems, where signals from local field potentials are excluded in the detection of neuron responses.

Brain functions arise from the coordinated activation of neuronal assemblies distributed across multiple brain areas. Each neuron receives several thousand inputs, which arrive at a coordinated temporal pattern to activate the neuron. Therefore, neural activity should be measured with a relatively high spatial resolution and a relatively high temporal resolution. Accordingly, to effectively measure neural responses, electrodes in a brain computer interface should provide a relatively large coverage with a relatively small pitch between the electrodes and the signal to noise (SNR) should be relatively high to achieve a relatively high BCI performance such as increased accuracy in decoding of brain signals.

Figure 2A:
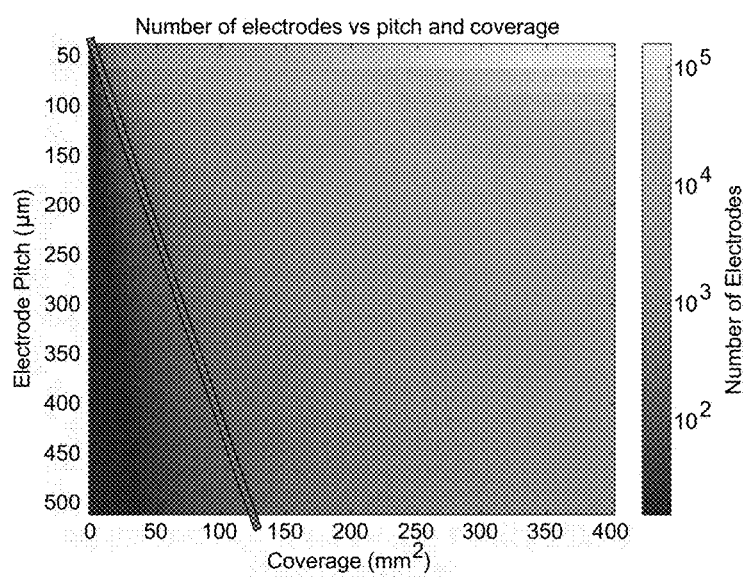
FIG. 2A shows relationships among a number of electrodes, pitches of the electrodes, and coverage by the electrodes.
Figure 2B:
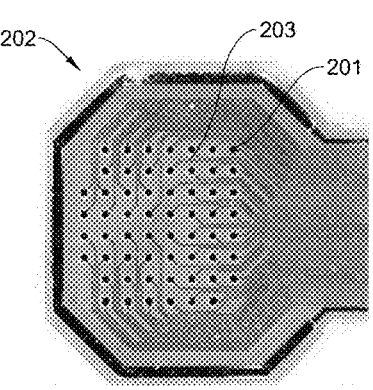
FIG. 2B shows a known circuit board having passive electrodes.

FIGS. 2A and 2B show the limitation of passive electrodes 201. In passive electrodes, each of the electrodes requires one output trace. FIG. 2A shows the relationships among the number of electrodes, pitches of electrodes, and coverage by the electrodes. The number of electrodes exponentially increases as the coverage increases. FIG. 2B shows a known electrode array 202 that includes passive electrodes 201. Each electrode 108 needs its own output trace 203 to transmit signals acquired by the electrode 108. To cover an increased area without sacrificing the density of electrodes or the pitch, the number of the electrodes would exponentially increase. While the number of electrodes increases exponentially, the amount of area available for output traces does not increase accordingly. As a result, a brain computer interface constructed with passive electrodes is not scalable to cover an increased area while still meeting the requirement of having a relatively high spatial resolution and a relatively high BCI performance.

In contrast, systems and methods described herein overcome the above described problems in the known systems and methods. Active electrodes are used, where signals from multiple electrodes are output via a shared output trace using a mechanism such as multiplexing. As a result, the coverage of the brain computer interfaces described herein is not limited by the space needed for output traces. The brain computer interfaces described herein are scalable to a desired dimension in the range direction and/or int the depth direction, without compromise in the quality of the signals detected from the electrodes. A front-end circuit is included at the site of each electrode to increase the SNR of the signals acquired by the electrode. Noise in the signals is further reduced by applying filtering such as kriging filtering. By transfer-printing, the electronic circuit of the brain computer interface is flexible and has a relatively small thickness, thereby conforming the circuit with the brain and reducing micro-motion of the brain computer interface relative to the brain. As a result, the electrical contact of the circuit with the brain and biocompatibility of the brain computer interface are increased. A scalable 3D brain computer interface is fabricated by rolling. Accordingly, the brain computer interfaces described herein are scalable in any direction and have increased biocompatibility, relatively high spatial resolutions, and relatively high BCI performance.

Figure 3A:
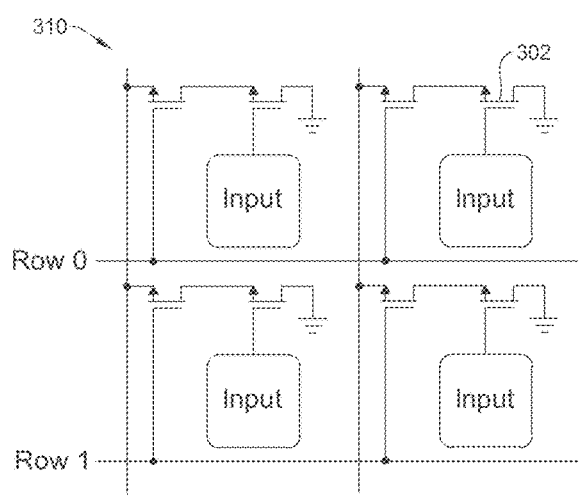
FIG. 3A is a schematic diagram of multiplexing.
Figure 3B:
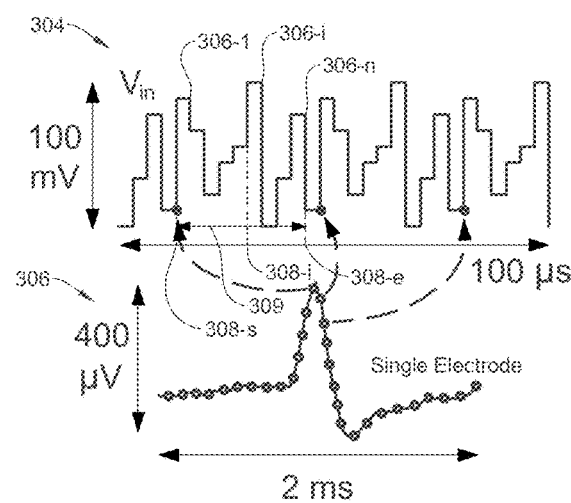
FIG. 3B shows that signals of a single electrode are derived from the multiplexed signals.

FIGS. 3A and 3B show a mechanism of multiplexing. FIG. 3A shows a schematic partial circuit diagram of an example multiplexer 310. FIG. 3B shows an example mechanism of de-multiplexing. In the example, signals from electrodes 108 are mixed in the time domain by switches 302. Switches 302 may be semiconductor switches, such as transistors. With the switching of switches 302, signals from electrodes are sampled one by one. For example, signals from electrode 1 are first sampled, followed by signals from electrode 2, and so on to electrode n. The process then goes back to electrode 1 and is repeated. The output signals 304 are a mixture of signals from all electrodes in the sampling order of the electrodes. For example, a sampling interval 309 of n electrodes starts from the starting time point 308-s to the end time point 308-e. The signal of output signals 304 at the starting time point 308-s corresponds to the signal 306-1 of electrode 1. The signal of output signals 304 at a time point i corresponds to the signal 306-i of electrode i. The signal of output signals 304 at the end time point 308-e corresponds to the signal 306-n of electrode n. Output signals 304 from the multiplexer 310 may be sorted to derive signals 306 of a single electrode 108. For example, signals at the starting time points 308-s are sorted to signals 306-1 of electrode 1, signals at the time points i are sorted to signals 306-i of electrode i, and signals at the end time points 308-e are sorted to signals 306-n of electrode n.

In the example, the switching frequency of switches 302 are selected to be relatively much greater than the frequency of signals 306 detected by electrodes 108 to preserve the information in the signals 306. For example, the switching frequency of switches 302 is in the ranges of 1 MHz or higher while signals 306 from electrodes 108 are in the range of 10 kHz or lower. The multiplexed electrodes share output traces 112, thereby significantly reducing the number of output traces 112 needed in the brain computer interface 102. Referring back to FIG. 1B, in the example, the shank 104 includes 32 electrodes. The 32 electrodes share output traces. The shank 104 has 8 I/O pads, 7 of which are shared across shanks 104. The remaining I/O pad is a single analog output shared by all 32 electrodes using a multiplexing factor of 32:1 in the multiplexer 310. A multiplexing factor is the number of electrodes that are multiplexed by a multiplexer. As a result, the number of output traces required per electrode is reduced by a factor of 32, compared to passive electrodes 201. By multiplexing, the number of output traces in the brain computer interface 102 is significantly reduced. Accordingly, electrodes 108 may be scaled to increase the coverage without causing spatial constraints for output traces 112.

Figure 15A:
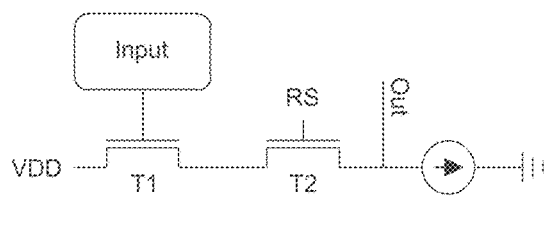
FIGS. 15A and 15B show multiplexing-supporting architecture.

Multiplexing may be based on voltage sensing (see FIGS. 10 and 15A described later). In some embodiments, multiplexing is based on current sensing (see FIG. 15B described later). Current-sensing multiplexing may have a reduced aliased noise, compared to voltage-sensing multiplexing. A correlated double sampling circuitry may be integrated in a current-sensing multiplier to reduce noise in the sample signals.

In some embodiments, instead of time domain multiplexing (TDM), other mechanisms of multiplexing are used. For example, a code-division multiple access (CDMA) is used in multiplexing. In CDMA, signals from electrodes are combined with a pseudo-random code known to the transmitter and the receiver. The combined signals may be separated using the pseudo-random code. CDMA has a reduced aliased noise, compared to TDM.

Figure 4:
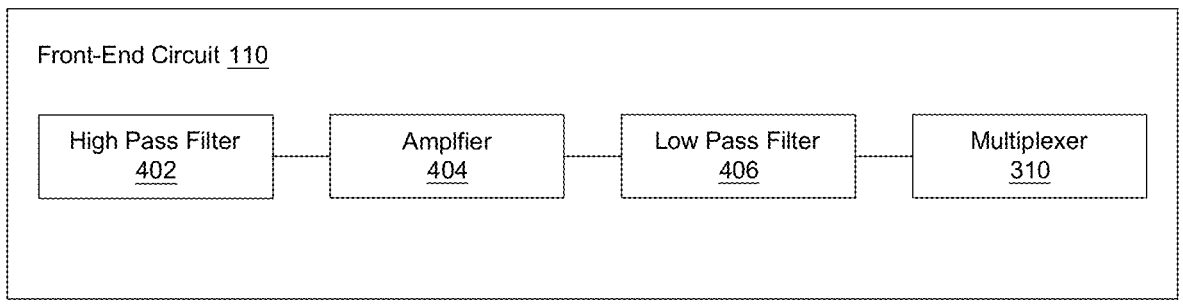
FIG. 4 is a schematic diagram of one suitable embodiment of a front-end circuit for an electrode.

The switching in a multiplexer introduces noise to signals of electrodes. To reduce the noise, a front-end circuit is included at the site of electrodes, thereby increasing the SNR of the signals. FIG. 4 is a schematic diagram of an example front-end circuit 110.

In the example embodiment, the front-end circuit 110 includes a high pass filter 402, an amplifier 404, and a low pass filter 406. The front-end circuit 110 further includes a multiplexer 310 configured to multiplex signals from multiple electrodes. Two major causes of noise in multiplexing are thermal noise and/or flicker noise from the semiconductor switches in multiplexing and aliased noise due to limited sampling frequency of the multiplexer 310. Signals enter the pixel 106 are filtered by the high pass filter 402 to remove direct current (DC) offsets. The filtered signals are then amplified by the amplifier 404. DC offsets are removed before the amplification to prevent the signals from exceeding the ranges in the amplifier 404 and thus to prevent damage to electronic components of the amplifier 404. Signals output from the amplifier 404 are filtered by the low pass filter 406 to reduce signals outside the frequency range corresponding to brain signals, which is 30 kHz or less, thereby reducing the aliased noise. Aliased noise is caused by signals in the relatively high frequency range being aliased or folded into the frequency range of the sampled signals, which is limited by the Nyquist frequency or one-half of the sampling frequency. Signals output from the low pass filter 406 are input into the multiplexer 310. In some embodiments, the front-end circuit 110 includes a buffer (not show) positioned between the low pass filter 406 and the multiplex 310. Signals output from the law pass filter 406 are buffered by the buffer and then input into the multiplex 310 for multiplexing.

A low pass filter includes a resistor in series with the input signals and a capacitor in a parallel with the input signals. In the example embodiment, to reduce the size of the resistor, the output resistance of the upstream circuit of the low pass filter 406, such as the high pass filter 402 and/or the amplifier 404, is the resistance used in designing the low pass filter 406, thereby eliminating the need of a separate resistor for the low pass filter 406.

In the example embodiment, the thermal noise and/or flicker noise of semiconductor components in the high pass filter 402 may be reduced by selecting a capacitor having a relatively high capacitance. The capacitor may be selected to have a capacitance as large as allowable by the area for the front-end circuit 110, e.g., an area of 50 μm by 50 μm minus the space saved for other electronic components in the front-end circuit 110.

In the example embodiment, the high pass filter 402 includes a resistor having a relatively high resistance. A relatively large resistance is used such that the high pass filter 402 has a relatively low cutoff frequency. There are neural signals of interest close to ~10 Hz. The relatively low cutoff frequency of the high pass filter 402 facilitates acquisition of neural signals that have frequencies in the range approximately 1 Hz or greater. Accordingly, a resistor having a relatively large resistance lowers the cutoff frequency of the high pass filter 402 such that local field potentials in the range of 1 Hz-250 Hz are captured by the brain computer interface 102. In contrast, in known BCI technologies, the high pass filter has a cutoff frequency above this range due to the difficulties in including a large resistor in a small area of the circuit.

In the example embodiment, the relatively large resistance is provided by semiconductor devices 1102, e.g. semiconductor devices M1 and M2 (see FIG. 11 described later). A relatively high resistance is difficult to accurately model using semiconductor devices. A bias voltage of the semiconductor devices 1102 are tuned to adjust the resistance. As a result, a relatively low cut-off frequency of the high pass filter 402 such as 0.1 HZ is achieved, thereby acquiring the entire spectrum of brain signals.

In the example embodiment, the front-end circuit 110 includes other components (not shown) such that each shank 104 provides a single output to the downstream circuit (not shown). The signals output from the brain computer interface 102 are transmitted to the BCI computing device 114 for further processing, such as de-multiplexing, filtering, analysis. The signals may be applied with kriging filters to reduce noise, such as noise in local field potentials (LFP). Compared to other filtering mechanisms such as spline smoothing, kriging filtering is advantageous in optimally adapting the filtering to the spatial statistics and SNR of LFPs in reducing noise in LFPs, thereby increasing the accuracy of the data.

FIGS. 5A-5B show that the circuit design of pixels 106 is optimized to be suitable for the brain computer interfaces 102 to be directly interfaced with or insert on and/or into the brain of a subject. FIG. 5A shows the matrix of an example brain computer interface 102. FIG. 5B is a comparison of the brain computer interface 102 with known brain computer interface 102.

In the example embodiment, the circuit design of the front-end circuit 110 is optimized by limiting circuit parameters of the front-end circuit 110 to meet predetermined thresholds. Example circuit parameters include power consumption in an area, input referred noise, and the bandwidths of the filters 402, 406 of the front-end circuit 110. The input referred noise may be specified with respect to a frequency range. The levels of input referred noise in the frequency ranges of 1-10 kHz are below 10 µV (see FIG. 5A). The 3 dB high pass filter frequency is 0.1 Hz. The 3 dB low pass filter frequency is 10 kHz. A 3 dB frequency is the frequency at which the signal has attenuated by 3 dB and is used to denote the bandwidth of a filter. Signals output from the brain computer interface 102 is in the range from approximately 0.05 Hz to 10 kHz, thereby covering the entire frequency range of brain signals, unlike known brain computer interface 502-$kn$ such as brain computer interface 502-$s$ and 502-$p$ (see FIG. 5B).

Thermal damage to the brain may occur from devices that cause a temperature increase greater than 2° C. The power density for implanted circuits recommended by the Association for the Advancement of Medical Instrumentation (AAMI) is limited to 40 mW/cm$^2$ or less, where power consumption of 40 mW/cm$^2$ causes an increase of 2° C. in the temperature of local tissue. In the example, one pixel 106 occupies an area of 50 µm by 50 µm. The power density limit of 40 mW/cm$^2$ corresponding to an area of 50 µm by 50 µm is a power consumption of 1 µW for that area.

In the known brain computer interface 502-$p$, although multiplexing is used, the known brain computer interface 502-$p$ is not designed to be directly inserted on the brain. The known brain computer interface 502-$s$ includes circuits at the site of electrodes and is designed to be directly inserted on the brain. The power consumption per channel of the known computer interface 502-$s$, however, is 6 µW, probably greatly exceeding the level of power consumption suitable for interfaces being directly inserted on and/or into the brain.

In contrast, in the example, the power consumption of brain computer interface 102 is 0.6 µW per channel or 0.6 µW for an area of 50 µm by 50 µm, well below the limit of 1 µW for that area. Accordingly, the brain computer interface 102 is scalable to increase the coverage, covers the entire frequency spectrum of brain signals, has a relatively high SNR, and is suitable for being inserted on the brain.

Figure 6A:
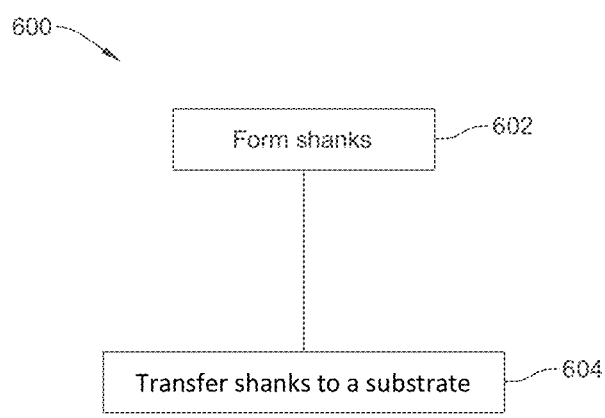
FIG. 6A is a flow chart of an embodiment of a method of fabricating a brain computer interface.
Figure 6B:
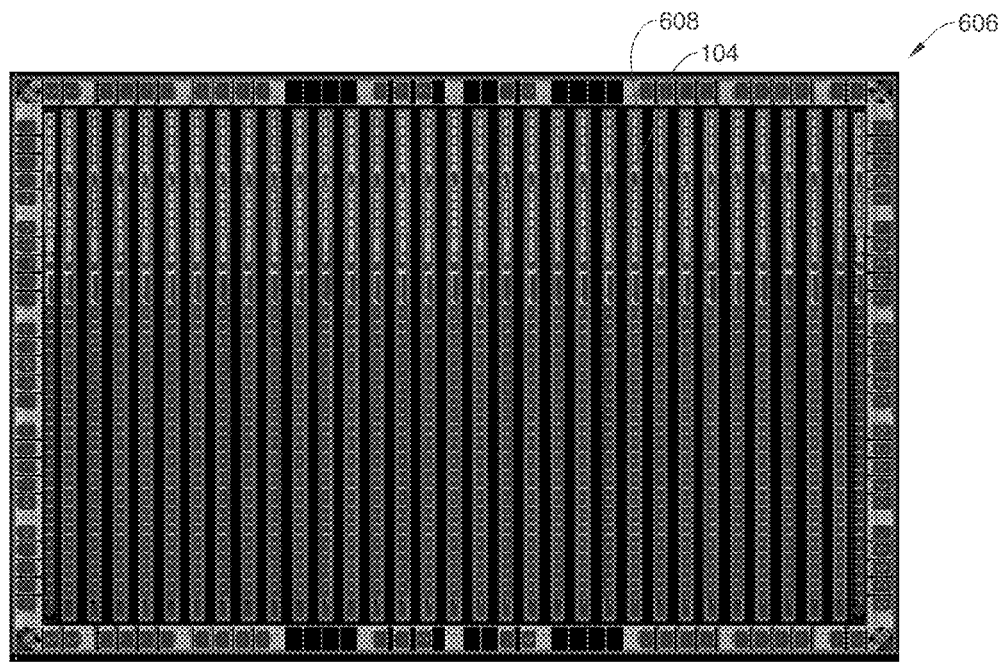
FIG. 6B shows a die before the shanks in the die are transferred.

FIG. 6A is a flow chart of an example method 600 of fabricating a brain computer interface. In the example embodiment, the method 600 includes forming 602 shanks. Example shanks are shanks 104 described herein. The method 600 further includes transferring 604 the shanks to a substrate. Shanks 104 may be manufactured in a die 606 by a foundry. A seal ring 608 may be placed around each individual shank 104 (see FIG. 6B). The seal ring 608 provides a barrier to prevent mechanical cracks from travelling into the shank 104 and causing damage to the electronics in the shank 104. The shanks are removed from the die 606 and transferred to a substrate. The substrate is a polymer substrate such as polyimide. The substrate is flexible and also provides insulation for the circuits. In some embodiments, shanks are transfer-printed (see FIGS. 26A and 26B described later), where the thickness of the electronic circuit is reduced and the flexibility of the electronic circuit is increased. A flexible circuit conforms to the irregular exterior shape of the brain, thereby increasing the electrical contact with the neurons and reducing micro motion or shifting of the electronic circuit relative to the surrounding tissue. Micro motion may cause strain-related damage to neurons. Accordingly, a transfer-printed brain computer interface 102 provides increased electronic performance while reducing potential damage to the brain. In some embodiments, a chip thinning mechanism is used, where the backside of the circuit is ground down to reduce the thickness of the circuit. Transfer-printed circuits have a smaller thickness than circuits thinned with the chip thinning mechanism.

In the example embodiment, a 3D brain computer interface 102 is fabricated by rolling (see FIGS. 25A-25G described later). An elastomeric layer such as a PDMS layer is applied to an array of shanks at the base region of the array. The array of shanks is formed into a 3D shape by rolling the elastomeric layer. In some embodiments, the tip of the shank 104 is tapered with a non-zero tip angle. A tapered tip facilitates the insertion of the brain computer interface 102 on the brain and reduce tissue damage from the insertion. In other embodiments, the shanks are partially stiffened by bonding the shanks with a biodegradable layer positioned approximate an insertion end of shanks 104 (see FIG. 26C described later). The 3D brain computer interface 102 may be a single-piece device. A single-piece device is advantageous in maintaining the integrity of the device, compared to a multi-piece device, where connections between separate components may be impaired from transportation, motion, or long-term use of the brain computer interface.

The dimension of the 3D brain computer interface 102 is scalable to a desired dimension in the range direction and/or the depth direction. The shanks 104 having a one-dimension array, such as 32 by 1, are described for illustration purposes only. The shanks 104 may be in a two-dimensional (2D) array. The dimension of the shank 104 may be adjusted by adjusting the array 105 of pixels in the shank 104 to an array of a desired dimension. The area covered by the shanks 104 may be expanded in the range direction by distributing the shanks on a surface along a length direction and/or a width direction of the shanks 104. The shanks 104 may be expanded in the depth direction by stacking the shanks. The expansion schemes described herein may be in any combination.

Figure 7:
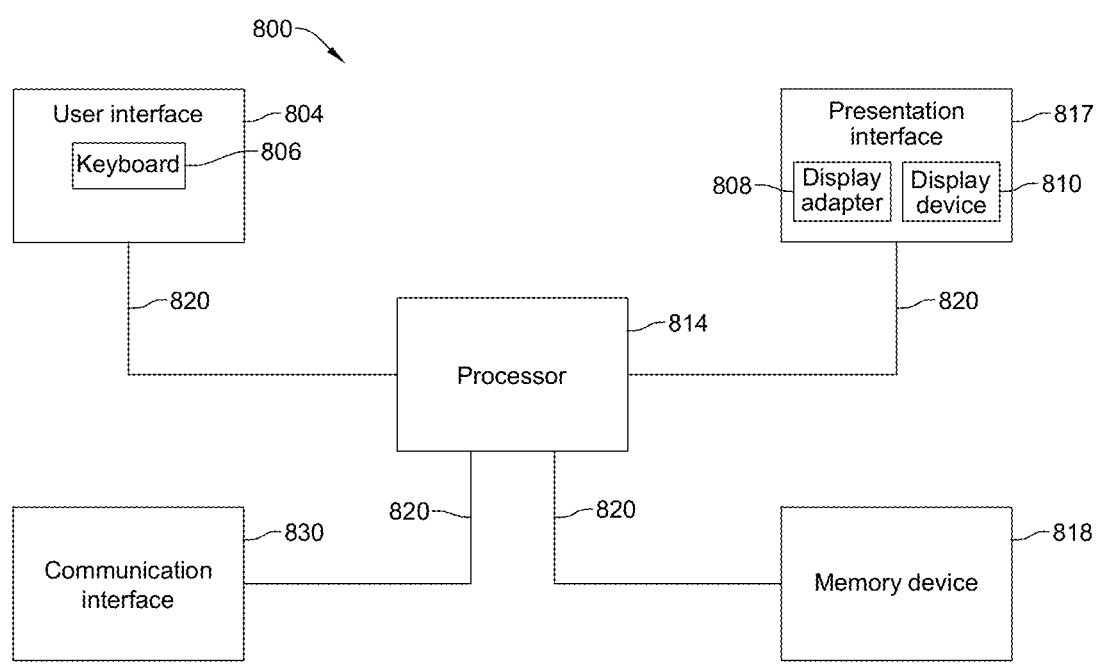
FIG. 7 is a block diagram of an embodiment of a computing device.

BCI computing device 114 described herein may be any suitable computing device 800 and software implemented therein. FIG. 7 is a block diagram of an example computing device 800. In the example embodiment, computing device 800 includes a user interface 804 that receives at least one input from a user. User interface 804 may include a keyboard 806 that enables the user to input pertinent information. User interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the example embodiment, computing device 800 includes a presentation interface 817 that presents information, such as input events and/or validation results, to the user. Presentation interface 817 may also include a display adapter 808 that is coupled to at least one display device 810. More specifically, in the example embodiment, display device 810 may be a visual display device, such as a cathode ray tube (CRT), a liquid crystal display (LCD), a light-emitting diode (LED) display, and/or an "electronic ink" display. Alternatively, presentation interface 817 may include an audio output device (e.g., an audio adapter and/or a speaker) and/or a printer.

Computing device 800 also includes a processor 814 and a memory device 818. Processor 814 is coupled to user interface 804, presentation interface 817, and memory device 818 via a system bus 820. In the example embodiment, processor 814 communicates with the user, such as by prompting the user via presentation interface 817 and/or by receiving user inputs via user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are example only, and thus are not intended to limit in any way the definition and/or meaning of the term "processor."

In the example embodiment, memory device 818 includes one or more devices that enable information, such as executable instructions and/or other data, to be stored and retrieved. Moreover, memory device 818 includes one or more computer readable media, such as, without limitation, dynamic random access memory (DRAM), static random access memory (SRAM), a solid state disk, and/or a hard disk. In the example embodiment, memory device 818 stores, without limitation, application source code, application object code, configuration data, additional input events, application states, assertion statements, validation results, and/or any other type of data. Computing device 800, in the example embodiment, may also include a communication interface 830 that is coupled to processor 814 via system bus 820. Moreover, communication interface 830 is communicatively coupled to data acquisition devices.

In the example embodiment, processor 814 may be programmed by encoding an operation using one or more executable instructions and providing the executable instructions in memory device 818. In the example embodiment, processor 814 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Figure 8:
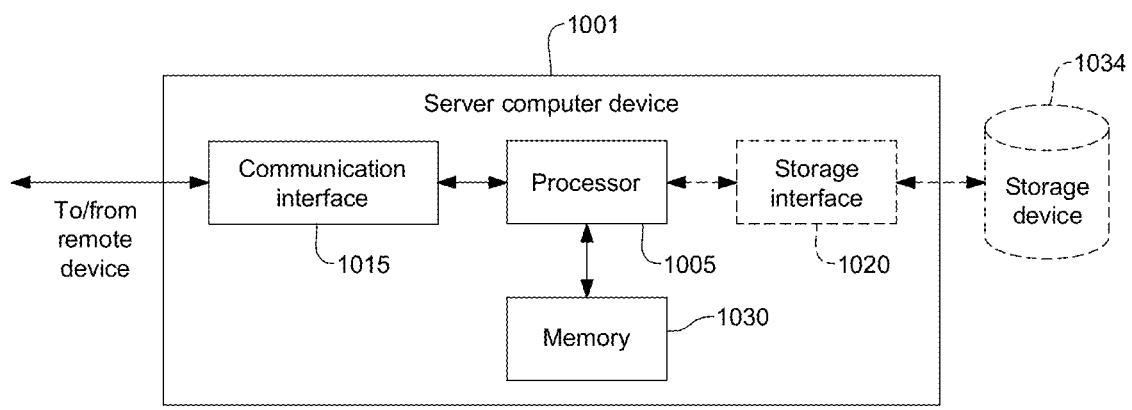
FIG. 8 is a block diagram of an embodiment of a server computing device.

FIG. 8 illustrates an example configuration of a server computer device 1001 such as BCI computing device 114. Server computer device 1001 also includes a processor 1005 for executing instructions. Instructions may be stored in a memory area 1030, for example. Processor 1005 may include one or more processing units (e.g., in a multi-core configuration).

Processor 1005 is operatively coupled to a communication interface 1015 such that server computer device 1001 is capable of communicating with a remote device or another server computer device 1001. For example, communication interface 1015 may receive data from brain computer interface 102 or another BCI computing device, via the Internet.

Processor 1005 may also be operatively coupled to a storage device 1034. Storage device 1034 is any computer-operated hardware suitable for storing and/or retrieving data. In some embodiments, storage device 1034 is integrated in server computer device 1001. For example, server computer device 1001 may include one or more hard disk drives as storage device 1034. In other embodiments, storage device 1034 is external to server computer device 1001 and may be accessed by a plurality of server computer devices 1001. For example, storage device 1034 may include multiple storage units such as hard disks and/or solid state disks in a redundant array of independent disks (RAID) configuration. storage device 1034 may include a storage area network (SAN) and/or a network attached storage (NAS) system.

In some embodiments, processor 1005 is operatively coupled to storage device 1034 via a storage interface 1020. Storage interface 1020 is any component capable of providing processor 1005 with access to storage device 1034. Storage interface 1020 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 1005 with access to storage device 1034.

EXAMPLES

Example 1

Brain computer interfaces (BCIs) provide clinical benefits including partial restoration of lost motor control, vision, speech, and hearing. A fundamental limitation of existing BCIs is their inability to span relatively large areas (>1 cm$^2$) of the cortex with fine (≤100 μm) resolution. One challenge of scaling neural interfaces is output wiring and connector sizes as each channel needs to be independently routed out of the brain. Time division multiplexing (TDM) overcomes this by enabling several channels to share the same output wire at the cost of added noise. Systems and methods described here leverage a 130-nm CMOS process and transfer printing to design and simulate a 384-channel actively multiplexed array, which minimizes noise by adding front end filtering and amplification to every electrode site (pixel). The pixels are 50 μm×50 μm and enable recording of all 384 channels at 30 kHz with a gain of 22.3 dB, noise of 9.57 !IV rms, bandwidth of 0.1 Hz-10 kHz, while only consuming 0.63 μLW/channel. The systems and methods described herein may be applied broadly across neural interfaces to create high channel-count arrays and ultimately improve BCIs.

I. INTRODUCTION

Brain computer interfaces (BCIs) are used clinically to restore partial motor function, speech, vision, and hearing to patients. The neural populations targeted by BCIs may span mm² to cm², while the individual neurons that constitute these populations exist on the scale of 10 s-100 s of μm. A neural interface should span in the range of mm² to cm² with individual electrode resolution of 10-100 μm in order to capture targeted neural populations at a scale approaching the single neuron level. However, existing neural interfaces are limited in the number of recording sites due to electrode wiring, resulting in a tradeoff between coverage and density. Active arrays address this limitation by adding a transistor at each electrode to enable time division multiplexing (TDM), which increases the number of channels without increasing the number of output wires. A primary limitation of TDM, however, is the increased noise added to the signal due to thermal noise aliasing, which decreases the signal-to-noise ratio (SNR) and thus BCI performance.

An approach to overcome this increased noise is to add an amplifier and anti-aliasing filter before the multiplexing transistor, which improves SNR by increasing the signal amplitude and reducing aliased noise. This is achieved by placing an amplifier and filters beneath or adjacent to the electrode, which limits the circuit area to 100-10,000 μm². This spatial constraint poses significant limitations on circuit complexity due to the area required to create low noise, bandpassed output signals. Additionally, thermal damage to the brain may occur in devices that cause a >2° C. temperature rise to the surrounding tissue. The power density value for implanted circuits recommended by the Association for the Advancement of Medical Instrumentation (AAMI) was derived from experiments in muscle tissue, which demonstrated that a power density of ~40 mW/cm² caused a 2° C. increase in local tissue temperature. This power density corresponds to a power consumption of 1 μW for a 50 μm×50 μm area.

The design and simulation of a low power intracortical electrode array designed in a 130-nm CMOS silicon-on-insulator (SOI) process are provided. The array includes twelve shanks with 32 electrodes per shank for a total of 384 channels, all of which may be sampled at up to 30,000 samples per second (SPS) to accommodate both local field potential (LFP) and action potential (AP) recordings. Each electrode is equipped with a high pass filter (HPF), amplifier, low pass filter (LPF), buffer, and multiplexing transistor beneath the sensing electrode in a 50 μm×50 μm "pixel" area. The description includes the design of the pixel circuit, followed by the simulated performance of the pixel's noise, gain, operating frequency, bandwidth, and power consumption.

II. ARRAY OVERVIEW & PIXEL ARCHITECTURE

A. Array Design and Fabrication Plan

Figure 9A:
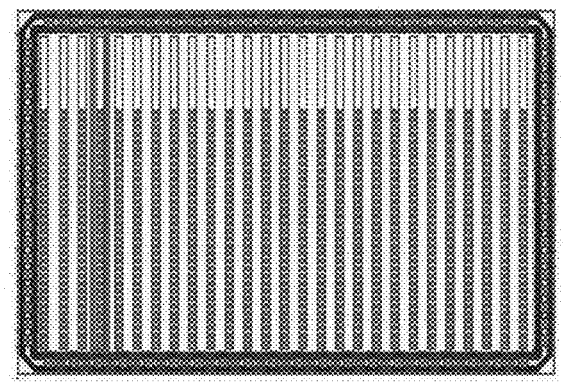
FIG. 9A shows the top-level layout of the CMOS die. 27 shanks are aligned in a row. A single shank to be transfer printed is highlighted in magenta.

The design is shown in FIG. 9A. Shanks are designed on a 10 mm² silicon die in a 130-nm, 1.2V, 6-metal layer SOI process. Each shank has 32 electrodes arranged in a single column with a 50 μm pitch and an overall shank size of 70 μm×2.4 mm. Each shank has 8 I/O pads, 7 of which are shared across shanks. The remaining I/O pad is the single analog output shared by all 32 electrodes using a 32:1 in-pixel multiplexer (MUX). Thus, the number of traces required per electrode is decreased by a factor of 32× as compared to passive electrodes. This enables electrode arrays to scale in channel-count beyond limitations imposed by individual electrode wiring.

Figure 9B:
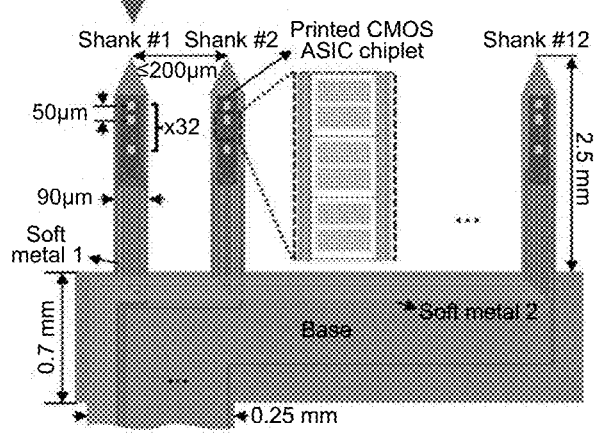
FIG. 9B shows that a final device including 12 shanks transfer printed onto a polyimide substrate. The shank from the die shown in FIG. 9A is highlighted. Three pixels are shown in the inlet on shank #2.

Once fabricated from the CMOS foundry (FIG. 9A), shanks are released from the bulk silicon using transfer printing to selectively remove only the SOI layer, silicon device layer, and the 6 metal/insulation layers, which total to a thickness of 12 μm. The shanks are then printed onto a polyimide substrate where electrodes and IO pads are exposed followed by metal layer deposition to route the signals in/out of the shank. Finally, the shape of the shank is defined by etching the polyimide substrate and the array is released from the substrate (FIG. 9B). Electrodes are located on the top metal layer, while electronics sit beneath the electrode. The rectangular electrode may be customized during post processing to range from 10 μm-38 μm per side by adjusting the insulation layer.

B. Circuit Overview

Figure 10:
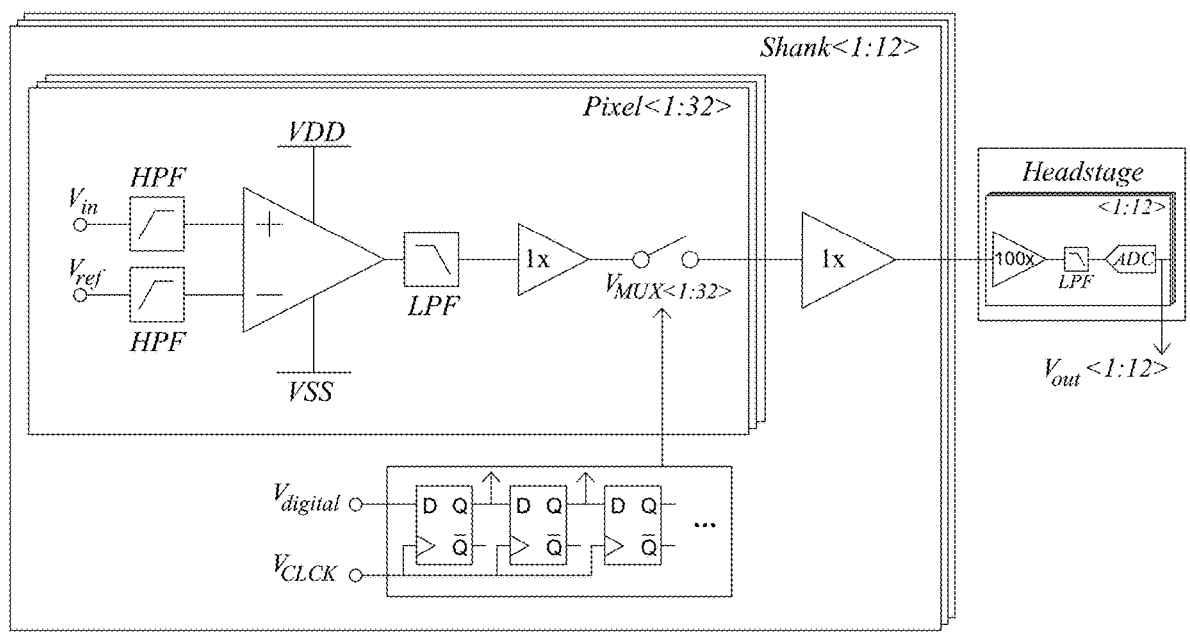
FIG. 10 is a schematic diagram of a circuit overview. In each of the 32 pixels, the signal and reference are high pass filtered before differential amplification followed by a low pass filter (LPF), buffer, and multiplexer. The signal is then buffered to create a single output/shank. Digital controls on the shank generate the MUX signal based on two digital inputs. The output of the shanks is then routed to a headstage where the signals undergo further buffering, amplification, filtering, and analog-to-digital conversion.

An overview of the circuit is shown in FIG. 10. The signal enters the pixel through $V_{in}$ while a reference signal enters through Vref. The reference may be selected as an electrode on the tip of the shank or the circuit ground, which is electrically connected to the brain. The signals are then high pass filtered at 0.1 Hz to remove DC offsets and are differentially amplified by a gain of 22.3 dB (13× magnitude). Next, the output is low pass filtered with an adjustable −3 db point of 10 kHz-30 kHz. The signal is then buffered and sampled using a MUX. The MUX control signal is generated by on-shank digital logic, which is controlled by two digital signals. A final buffer drives the single output per shank to the headstage where the signal is further buffered, amplified, and digitized using a 12-bit ADC. Lastly, the digital outputs travel to a computer for software de-multiplexing and analysis.

C. High Pass Filter

Figure 11:
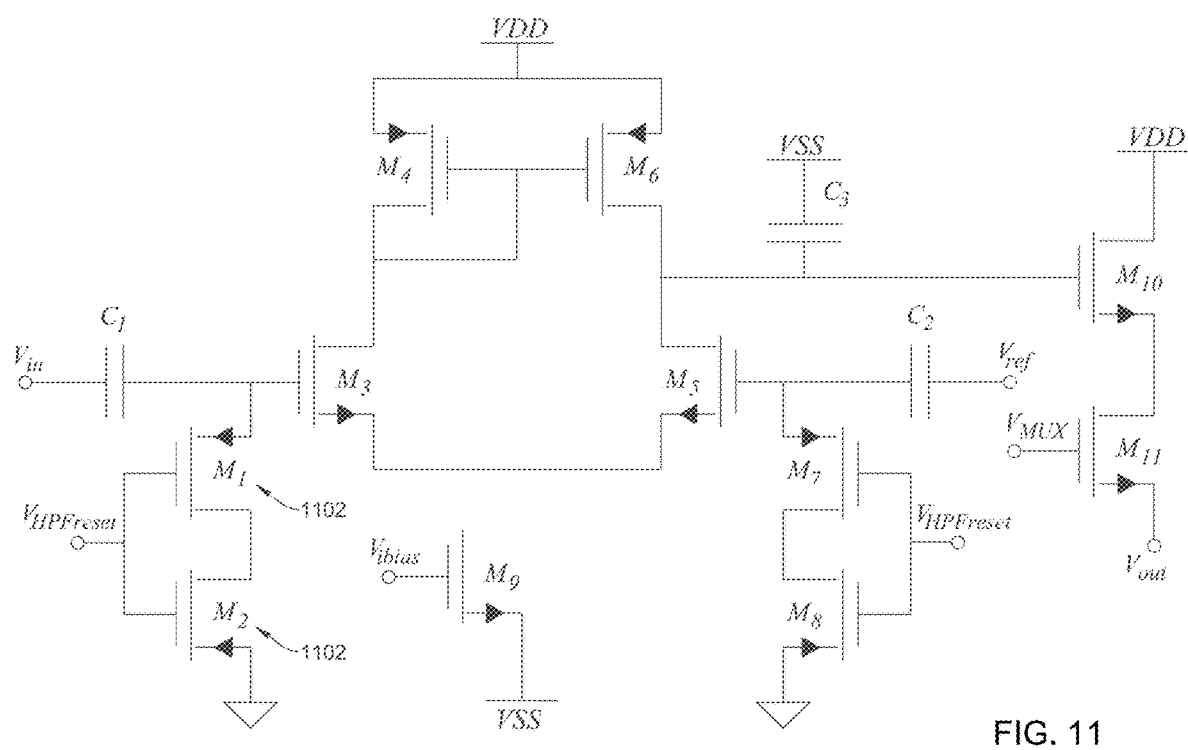
FIG. 11 shows a transistor level pixel schematic. The signal and reference enter the pixel and pass through a high pass filter (HPF) before entering a differential amplifier. The output passes through a LPF and is buffered before multiplexing.

A transistor level schematic of the pixel is shown in FIG. 11. A key challenge of the area-constrained design is the HPF due to the large values of resistance and capacitance required to achieve a −3 db cutoff of 0.1 Hz. The capacitor should be as large as possible to lower noise and minimize any DC offsets that may arise from leakage current across the resistor. However, the capacitor with the lowest leakage current per area and highest capacitance per area available in this process node is the metal-insulator-metal (MIM) capacitor. Using MIM capacitors, the maximum capacitance achieved for two in-pixel capacitors is 1.2 pF per capacitor. Thus, a 1.3 TΩ value resistor is required to obtain a −3 db cutoff of 0.1 Hz. The 1.3 TΩ resistor was created using two PMOS devices biased by $V_{HPFreset}$ to be in the cutoff regime. The two PMOS devices form reverse-biased diodes with their resistance determined by their source-drain leakage current. The devices' width-to-length ratio (W/L) was optimized to produce the 1.3 TΩ resistor. However, this high resistance is difficult to accurately model using CMOS resistors. To overcome this challenge, $V_{HpFreset}$ may be used to tune the resistance post-fabrication by adjusting the source-drain leakage current to accommodate discrepancies between the simulated and actual value of the resistance.

The high resistance poses an additional challenge—any leakage current (the dominant source being the gate-source leakage of $M_3$ or $M_5$) produces a DC offset between the input into the differential amplifier and ground equal to the leakage current ($I_{leak}$) multiplied by the equivalent resistance of the reverse biased PMOS diodes (~1.3 TΩ). To overcome this issue, $V_{HPFreset}$ was periodically switched to turn the PMOS devices on to re-bias the node to ground.

When the PMOS devices are on, their resistance drops to several hundred ohms and thus the node voltage resets rapidly. For additional design optimization post-fabrication an optional connection to the drain of $M_2$ and $M_8$ was added to tune the DC input value to the differential amplifiers.

D. Differential Amplifier

The differential amplifier was selected due to its high common mode rejection ratio (CMRR). The NMOS differential amplifier was selected due to sizing constraints, which prohibited a PMOS design with equivalent transconductance. During common mode operation, the gate voltages of $M_3$ and $M_5$ are equal and the bias current through $M_9$ (set by $V_{ibias}$) is equally divided amongst the two halves of the differential amplifier. However, a change in the gate voltage of $M_3$ forces a proportional and opposite current change in the drain of $M_5$, which in turn changes the voltage on the drain of $M_5$ and produces a gain equal to:

$$A_{dm} = g_{m5}(r_{o5} \| r_{o6}) \quad (1)$$

where $g_{m5}$ is the transconductance of $M_5$ and $r_{o5}/r_{o6}$ are the output resistances of $M_5$ and $M_6$, respectively. The parallel combination of the output resistances of $M_5$ and $M_6$ is equal to the inverse of the sum of the output transconductances ($g_o = 1/r_o$). The total differential mode gain is thus given by:

$$A_{dm} = \frac{g_{m5}}{g_{o5} + g_{o6}} \quad (2)$$

and may be simplified by g o =I d A. as:

$$A_{dm} = \frac{g_{m5}}{I_d(\lambda_{m5} + \lambda_{m6})} \quad (3)$$

where $\lambda_{m5}$ and $\lambda_{m6}$ are the channel-length modulation parameters for $M_5$ and $M_6$, respectively.

To set the gain, the W/L ratios of all transistors in the differential amplifier were optimized, as well as the bias current. During device operation, the bias current is controlled by an on-shank 1:32 current minor (not shown) and may be tuned by adjusting $V_{ibias}$ indirectly. By adjusting the bias current, the bandwidth of the differential amplifier may be tuned.

E. Low Pass Filter

The LPF is used for removing aliased thermal noise in multiplexed signals and was designed to range in −3 dB from 10 kHz-30 kHz to enable neural spiking recording. The LPF is formed by the output impedance of the differential amplifier and C3. The −3 dB point of the filter is given by:

$$f_{-3dB} = \frac{1}{2\pi(r_{o5} \| r_{o6})C_3} \quad (4)$$

and may be simplified by plugging in the value of $(r_{o5} \| r_{o6})$ derived above as:

$$f_{-3dB} = \frac{I_d(\lambda_{m5} + \lambda_{m6})}{2\pi C_3}. \quad (5)$$

Thus, the current may also be used to adjust the −3 dB point of the LPF. To ensure the range of operation was within the current limits imposed by power density constraints, C3 was designed to be 7.5 pF using the largest capacitance per area capacitor available—the NMOS varactor. This device was not chosen for $C_1$ or $C_3$ due to the extreme sensitivity of the gate bias of $M_3$ and $M_5$ to leakage current. However, the output of the differential amplifier is less sensitive to leakage current. The varactor capacitance magnitude varies by less than 2% in the range of DC values of the output of the differential amplifier, which ensures low variation in −3 dB cutoff frequency of the LPF.

F. Source Follower & Multiplexer

To create a low output impedance and preserve the −3 dB point of the LPF, the output of the differential amplifier is buffered by a source follower formed by $M_{10}$ and a current source located on the shank (not shown) when the multiplexer ($M_{11}$) is closed. The digital signal that samples the pixel ($V_{MUX}$) is unique to every pixel and is generated by an onshank shift register (FIG. 10). The output ($V_{out}$) is shared by all 32 pixels, as is the current source that completes the source follower circuit. The W/L values of $M_{10}$ and $M_{11}$ as well as the current value were optimized to maintain the gain of the source follower to be >0.9 and the 99.9% settling time between channels to be ≤1 μs. This settling time value was chosen to ensure the 32 channels could be sampled at 30 kilo-samples per second (kSPS) per channel, which requires a 960 kHz sampling rate and a settling time ≥1.04 μs. A final buffer on the shank (shown in FIG. 10, shared by all channels) drives the output of the shank.

III. SIMULATION RESULTS

Final optimization results are shown in Table 1 and were simulated using Cadence Virtuoso® and Spectra®. In all analyses, the W/L ratio values of transistors, current values, resistances, and capacitances were optimized to meet the design specifications. Table 1 contains the results of a mismatch and process corner Monte Carlo analysis with 2000 iterations, and a gaussian distribution of mismatch parameters of 4σ. The results are shown as an average ±standard deviation.

TABLE 1

| CIRCUIT PERFORMANCE | | |
|---|---|---|
| | Design | Simulation |
| Gain | >20 dB | 22.3 ± 0.8 dB |
| HPF-3dB | 0.1 Hz | 0.13 ± 0.001 Hz |
| LPF-3dB | 20 kHz | 10.6 ± 0.7 kHz |
| Noise (1 Hz-30 kHz) | <10 μΩ | 9.54 ± 0.3 μV |
| Noise LFP (1-300 Hz) | — | 5.49 ± 0.2 μV |
| Noise AP (300 Hz-6 kHz) | — | 4.06 ± 0.2 μV |
| Power consumption/ch | 1 μW | 0.63 ± 0.03 μW |
| Maximum MUX rate | 1 MHz | 1 MHz |

A. AC Analysis

Figure 12:
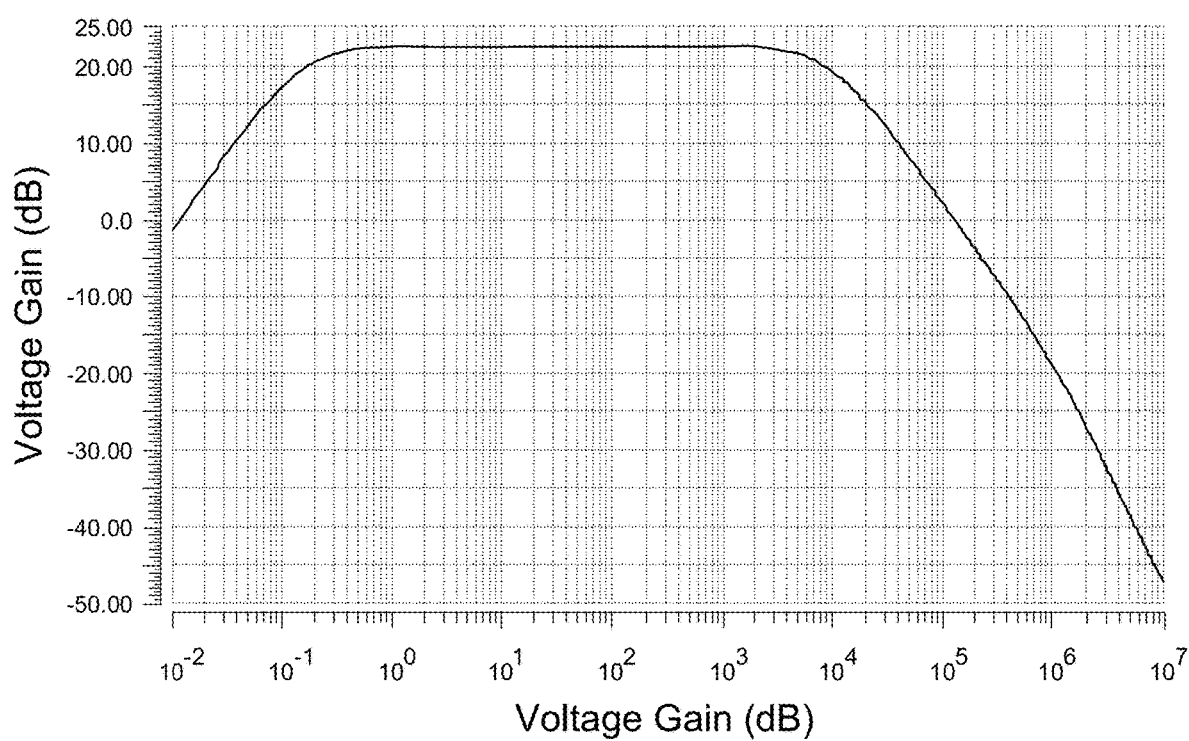
FIG. 12 illustrates the AC response of the differential amplifier using a current of 0.5 µA. The mid-band gain is 22.3 dB. The HPF −3 dB frequency is 0.13 Hz while the LPF −3 dB frequency is 10.6 kHz.

The AC response with a differential amplifier bias of 0.5 μA is shown in FIG. 12. The mid-band gain is 22.3±0.8 dB and was optimized to be as high as possible while keeping the noise low. A lower current produces a higher gain as shown in Eqn. (3) but increases thermal noise, which is the dominant noise source beyond 10 Hz. Additionally, if the current is too low, the bandwidth of the amplifier decreases (see Eqn. (5)) and may be less than 10 kHz, which may filter out neural signals. Lastly, the low voltage process (1.2V) limits the headroom of $M_6$ on the output node of the differential amplifier. Thus, 22.3 dB was selected based on simulation results. This value provides enough gain to send the signal to the head stage for further gain and minimize the overall contribution of circuit noise between the shank and the head stage on SNR.

The HPF optimization resulted in a −3 dB point of 0.13±0.001 Hz, which is high enough to remove DC offsets that arise from the electrode tissue interface and low enough to accommodate LFP recordings that contain information down to single Hz values. The HPF reset ($V_{HpFreset}$) eliminated the voltage drift in <10 μs and required switching after 1.57 s (0.63 Hz), which does not interfere with LFP recordings.

The value of C3 (FIG. 11) was set at 7.5 pF resulting in a LPF −3 dB frequency of 10.6±0.7 KHz at a bias current of 0.5 μA. The LPF −3 dB point may be tuned by adjusting the bias current of the differential amplifier and may range from 10-30 kHz. The increased bandwidth may enable finer reconstruction of AP to improve spike sorting.

B. Noise and Power

Noise analysis was performed using a noise source on the input ($V_{in}$) while grounding $V_{ref}$ (FIG. 10) and probing the output of the shank buffer. Noise optimization resulted in an input referred full bandwidth (1 Hz-30 kHz) noise of 9.54±0.3 μV rms, 5.49±0.2 μV rms in the LFP band (1 Hz-300 Hz), and 4.06±0.2 μV rms in the AP band (300 Hz-6 kHz).

The source follower current optimization resulted in a bias of 1 μA to achieve a maximum 99.9% settling rate between channels of ≤1 μs. This current was shared between all channels. The overall power consumption of the pixel was 0.63 μW with the differential amplifier at a 0.5 μA bias (0.6 μW from the pixel, 0.03 μW from the shared source follower).

C. Source Follower and MUX

A function of the source follower is to drive the output load quickly while maintaining a gain close to its ideal value of 1. To sample 32 channels at 30 kSPS, the output value of the pixel should settle to 99.9% of its final value in <1 μs. A Monte Carlo analysis was performed to determine the maximum DC difference between differential amplifier outputs of adjacent pixels. The average value was found to be 347 mV±30 mV with an absolute range of 250-450 mV. Thus, a 200 mV DC offset between adjacent pixels was used in sampling simulations. The current and W/L ratio of the source follower and MUX transistors in the pixel were optimized to settle within 99.9% of their final value within ≤1 μs with a 0.95 gain using a current of 1 μA. Initially, this source follower was designed to drive the output load of the connector and headstage, but the large output load (estimated as R=5 KΩ and C=20 pF) required an area larger than available in the pixel. Thus, adding an additional source follower to handle the output load on the base of the shank in addition to the in-pixel source follower enabled ≤1 μs switching between channels.

IV. DISCUSSION

The design and simulation of an actively multiplexed intracortical electrode array with 384 recorded channels are provided. The pixel design leverages TDM to enable scalable neural recording and decreases aliased noise by adding novel front-end filtering and amplification to the electrode site. The pixel achieves a 22.3 dB gain over a band of 0.1 Hz-10 kHz with noise <10 μV rms while consuming 0.63 μW/channel, which is less than the 1 μW/pixel area (40 mW/cm$^2$) recommended by the AAMI. This value may be decreased using a sampling rate lower than 30 kSPS/channel.

The front-end pixel design outlined in this work has 5-10× lower power consumption per channel than TDM-based active arrays with in-pixel amplification. Additional channels may be added to shanks by extending the length of the shank by 6.5× to 10 mm, which is the length of a pixel using a known method such as Neuropixel. Unlike the known pixel, channels in the systems and methods described herein may be actively multiplexed during recordings as opposed to a fixed selection before recording, which reduces the number of output wires by the multiplexing ratio (32). This scaling is enabled by the addition of in-pixel amplification and low pass filtering, which removes the TDM limitation of aliased noise. Overall, this architecture paves the way for significantly higher channel count neural interfaces and may be adapted broadly across devices including intracortical and RECoG arrays.

Example 2

Neuro-CROWN: Optimized ultra-flexible CMOS electrode arrays for 3D, low-noise neural interfaces A fundamental obstacle to understanding neural circuit interactions is the difficulty of observing and manipulating the activity of large, distributed populations of neurons in freely behaving animals. While electrophysiological techniques have been the gold standard for monitoring brain activity, the electrode arrays used in these techniques cannot easily be scaled to high channel counts. Large throughput electrophysiology requires active electrode arrays, in which electrodes and electronics are integrated on the same substrate. However, this approach introduces noise into the recording, primarily due to multiplexing without amplification and anti-alias filtering—there is insufficient space and power for a full amplifier and filter at every electrode. Current-generation active arrays such as the Neuropixels probes may record from only a subset of the electrodes on the array at one time. Low noise is needed for real-time systems that require a high signal-to-noise ratio (SNR), such as brain machine interfaces for motor and speech prostheses and closed-loop recording and stimulation devices used to treat neurological disorders. Systems and methods described herein provide arrays that simultaneously have high resolution, large spatial coverage, and a high SNR.

From a spatial perspective, the maximum recording distance between an extracellular electrode and a neuron is ~150 μm. Flexible, three-dimensional (3D) electrode arrays are needed that may interface with high-density neuronal circuitry in the millimeter-thick cerebral cortex at sub-150 μm distances. The softness of implanted neural probes is also recognized as an attribute needed for maintaining high signal quality over long periods of time and for reducing tissue injury and irritation. Therefore, flexible, low-noise, active electrode arrays are created by using a unique, ultra-flexible, complementary metal-oxide—semiconductor (CMOS)-based 3D neural interface called Neuro-CROWN (CMOS-based, rollable, low-noise neuroelectronics).

Aim 1: Optimize circuit and multiplexing strategies to improve active array SNR. The SNR is improved in actively multiplexed electrode arrays by utilizing two techniques: (1) ultra-sensitive, currentsensing (CS) circuit designs together with on-site filtering, which are simulated, fabricated and tested experimentally, and (2) novel multiplexing strategies such as code-division multiple access (CDMA) to reduce the aliased noise in active electrode arrays. These optimizations are tested in both in vitro and in vivo experiments.

Aim 2: Spatially denoise neural signals using kriging. Kriging—a linear prediction method from geostatistics—is implemented to remove instrumentation noise from local field potentials (LFPs). Linear filters are applied to spatially over-sampled LFPs and uncorrelated noise to yield noise-reduced cortical potentials. Unlike kernel- or spline-smoothing, kriging filters are optimally adapted to the spatial statistics and SNR of LFPs. Filters should also be updated to adapt to time-varying field statistics. Model optimization is well-suited to fixed-rank matrix approximations and parallel GPU computation, making online processing feasible. Using these tools, the data stream is separated into spatially-denoised LFPs and neuron spiking activity.

Aim 3: Develop an ultra-flexible, high-density, low-noise 3D active microelectrode array and validate it with chronic in vivo recording. A method, rolling of 2D soft electrode arrays (ROSE), is adapted to create optimized low-noise, 3D, active arrays with 2,048 simultaneously-measured channels. These Neuro-CROWN arrays include faradaic electrodes as small as 180 $\mu m^2$, with an electrode density of up to 1,152/$mm^3$. The shanks are ultra-thin (~10 µm) polymer shanks to reduce the insertion footprint and to optimize in vivo insertion in rodents. Further processes include optimization of the rolled configuration, substrate and encapsulation materials, thickness, shank profile, and temporary stiffening for insertion by in vitro characterization, chronic (3-month) in vivo tissue biocompatibility assessments, and evaluation of recording from the rodent brain.

Together, these improvements and optimizations enable active electrode arrays to record neural signals on a large scale and in 3D with high resolution and high signal-to-noise. These active array technologies are applicable to many types of neural interfaces, including both surface and penetrating electrodes. The improvements provided by this technology optimization enable dramatic increases in the performance of neural interfaces.

Significance

Brain functions such as perception, motor control, learning, and memory arise from the coordinated activation of neuronal assemblies distributed across multiple brain areas. While major progress has been made in understanding the response properties of individual neurons, circuit interactions remain poorly understood. In neural circuits, spike timing at the millisecond scale plays a critical role in shaping the flow of activity and synaptic organization. Each neuron receives several thousand inputs, which must arrive in a coordinated temporal pattern to depolarize the neuron. Spike timing is also critical in structuring interactions and in the flow of activity across brain areas. Hence, neuronal activity should be measured with sub-millisecond resolution, and electrophysiological techniques are the gold standard for such measurements. To isolate the activity of individual neurons through extracellular recordings, a multiplicity of densely spaced recording sites is also required. Because of the separation between the signal sources (neurons) and recording sites, each neuronal spike is simultaneously detected on multiple channels, but with different amplitudes that depend on the neuron's relative position. Electrodes with extremely dense contacts enable high-quality isolation of the activity of multiple neurons.

For all electrode arrays, the principal challenge is to achieve scale-up in a way that is minimally invasive. The key to achieving minimally invasive scale-up is through the use of active, flexible arrays, with multiplexing directly at each electrode site. Novel flexible semiconductor technology is used to develop flexible, active electrode arrays that enable simultaneous recording and stimulating from thousands of electrodes. Using time-division multiplexing (TDM), up to 1000 electrodes may be multiplexed to share a single output wire, since silicon transistors may switch at lOs of MHz while brain electrophysiology changes on the kHz timescale.

The challenge that has limited active arrays in known rigid Neuropixels is the increased aliased noise introduced by TDM at the electrode. Multiplexing without amplification and anti-alias (low-pass) filtering introduces additional noise in recordings due to aliasing (or folding) of high-frequency noise from the electrode, environment, and pixel circuitry (up to ~10 MHz) into the neural signal bandwidth (1 Hz-10 kHz). This aliasing occurs at the multiplexer right at the electrode, where the conversion from continuous time to discrete time occurs. This increased noise has limited the performance of Neuropixels. In high-density electrodes (pitch <50 µm), there is not enough room to fit an anti-aliasing filter at each electrode.

Neuropixels probes, therefore, do not utilize on-site multiplexing, and instead allow the user to select a subset of the electrodes (384 out of 960) for recording at any one time, to prevent aliased noise. Exactly which electrodes may be selected is constrained by the probe design. Further, to accommodate over 384 wires in the shank of the Neuropixels probe, the wires are very narrow and tightly spaced, increasing crosstalk and precluding electrical stimulation. Adopting the strategies described herein would reduce the number of wires required in the shank of the probe ten-fold to ~40, and enable simultaneous recording and stimulation.

Noise Performance. While incorporating an unprecedented, soft 3D form factor (FIG. 13), the performance of multiplexed arrays is improved. FIG. 14 is a comparison of performance of the arrays described herein with that of non-multiplexed silicon arrays, i.e. Neuropixels (FIG. 14). The signal to noise ratio (SNR) of Neuropixels arrays is sufficient for neuroscience research. The arrays described herein may obtain equivalent or larger SNR with a multiplexed array, thereby enabling dramatic scale-up to thousands of electrodes.

Circuit and system designs are optimized, which provides low-noise, multiplexed acquisition of neural signals from active arrays with thousands of electrodes. The optimized design allows all of the electrodes on active arrays to be sampled continuously, and permits multiplexed stimulation. The low-noise active arrays are developed using a unique ultra-flexible neural interface paradigm called Neuro-CROWN (CMOS-based, rollable, low-noise neuroelectronics).

Figure 13:
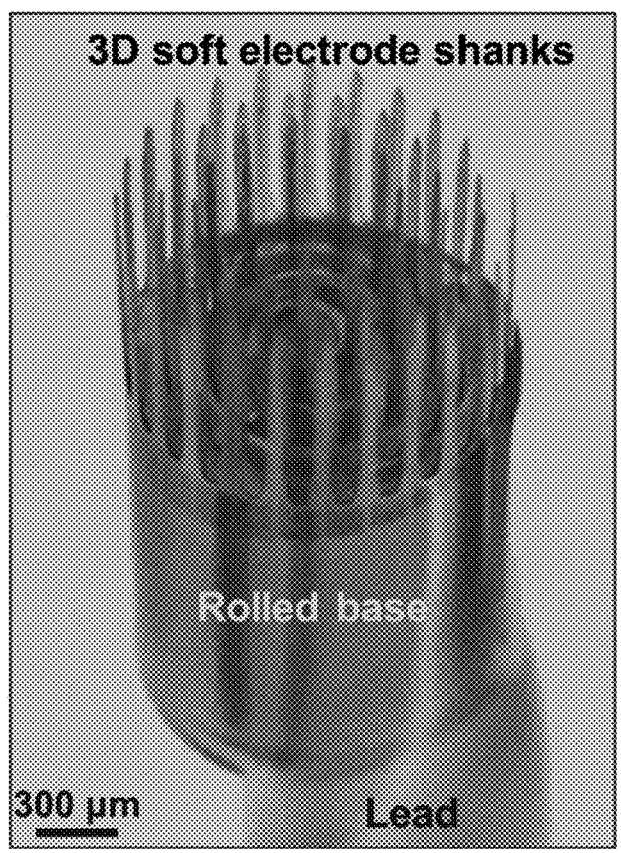
FIG. 13 shows an example prototype flexible, rollable 3D neural probe with 256 electrodes over 64 shanks.

Using this paradigm, active, 2D, soft electrode arrays are fabricated and rolled into 3D neural interfaces (FIG. 13). This method leverages the advanced capabilities and simplicity of semiconductor fabrication in 2D, and provides an easy solution to turning 2D flexible structures into 3D neural interfaces. The Neuro-CROWN arrays provide true 3D sampling of the brain, with nearly equal spatial resolution in all three dimensions. The arrays may sample from multiple cortical layers with multiple electrodes per penetrating shank, while simultaneously sampling equally well from multiple cortical regions. In this effort, the method, rolling of 2D soft electrode array (ROSE), is optimized to fabricate low-noise, active arrays with 2,048 simultaneously-measured electrodes, with the capability for tens of thousands of channels.

ASICs incorporated at the electrodes. Neuro-CROWN includes CMOS (Complementary Metal-Oxide-Semiconductor) ASICs (Application-Specific Integrated Circuits) in each shank of the electrode array. The ASIC in each shank multiplexes signals from the electrodes in a ratio of 32:1, while only requiring 6 external wire connections. Of these six external wire connections, five are shared among all the shanks. Therefore, only 69 wires are required to sample from 2,048 electrodes. This design allows scaling without wiring limitations.

Packaging and encapsulation. The CMOS ASICs are fabricated using an SOI (silicon on insulator) process. The bulk silicon substrate is removed and the ultra-thin silicon chiplets are transferred onto a flexible substrate. The silicon chiplets are encapsulated via the integrated thermally-grown SiO2 from the SOI process. Connections to the electrodes on the front side of the device are made using hermetically sealed VIAs (vertical interconnect access) through the SiO2. The back side of the ASIC is connected to wiring encapsulated in the flexible substrate, which may be made out of polyimide, or liquid crystal polymer (LCP), which has a relatively superior moisture barrier properties.

Minimal invasiveness. The devices described herein achieve minimal invasiveness through the use of ultra-thin (down to 2 μm thick), flexible CMOS circuits. Materials of the devices are selected to be sufficiently soft and flexible to yield implantable electrodes with pliability matching that of the brain. The selected materials may minimize differential "micro motion" between the probe and surrounding tissues, and reduce the strain-related damage and encapsulation that this micro motion may induce. Conventional semiconductors—usually brittle, inelastic materials—become ultra-flexible and pliable when made sufficiently thin. This property enables a new approach to creating pliable, minimally-invasive implantable neural probes. Systems and methods described herein use CMOS integrated circuits and render them flexible by extreme thinning.

Neural interfaces. High-resolution neural interfaces are increasingly important in therapeutic and prosthetic devices. The device technology described herein enables further device scaling, enabling higher resolution and powerful insights into brain function. Active devices may sample large volumes of the brain at high density and resolve single-neuron activity. Leveraging commercial CMOS manufacturing provides a practical pathway towards high-throughput neural interfaces, while dramatically reducing noise in the device.

In summary, systems and methods described herein optimize and disseminate implantable active electrode arrays for long-term in vivo use, with flexible electronics that are scalable in three dimensions and in channel count and resolution. The techniques for fabrication and in vivo testing of active electronics that readily scale to high channel counts enable flexible neural interfaces for a broad range of applications.

Description

Novel multiplexing optimizations and spatially denoise data through software are investigated. These techniques are validated first using multiplexed micro-electrocorticographic (μECoG) arrays. The noise reduction techniques are benchmarked against passive, non-multiplexed μECoG arrays in rat auditory cortex. The broad applicability of the noise-reduction techniques is demonstrated by applying the spatial denoising algorithms to data from Neuropixels arrays. Finally, these techniques are implemented in Neuro-CROWN: an innovative 3D, ultra-flexible, high-density soft penetrating electrode array to enhance the overall throughput and SNR of neural recordings.

Figure 15B:
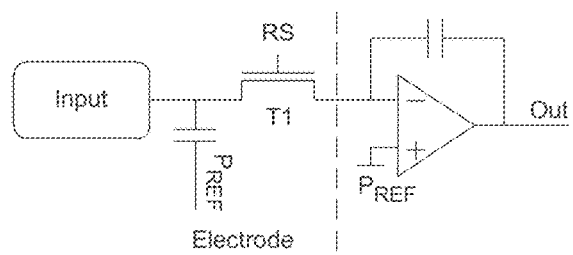

Current-sensing (CS) circuit design. Active multiplexed electrodes presently use a two transistor (2T) design with voltage-sensing at each electrode (the 'pixel') (FIG. 15A). To reduce aliased noise, multiplexed, CS circuit strategies are tested (FIG. 15B), on flexible CMOS electrode arrays. It has been demonstrated that recording neural signals from non-multiplexed electrodes using CS and achieved comparable SNR to voltage-sensing recording systems. This recording approach measures extracellular neural currents (rather than voltage) by integrating charge over the sampling period. This approach includes high channel count (64-256 channel) amplifiers that have extremely low-noise recording capabilities and are designed for multiplexed input signals. Current sensing is applied in the multiplexed, active electrode pixel (FIG. 15B). Charge integration at the capacitor in the pixel (FIG. 15B) reduces aliased noise. Acquisition circuits with up to 256 input channels, combined with active electrode arrays with 32:1 multiplexing, are used to record from up to 8,192 electrodes simultaneously on a single array. Custom recording circuitry may be included to increase the multiplexing ratio to further scale up the number of electrodes.

Correlated double sampling (CDS). Noise is further reduced by integrated CDS, which reduces 1/f noise, crosstalk, multiplexer charge injection, and kTC-noise. kTC-noise describes the total thermal noise power. CDS in the design is implemented by commercial, CS ICs in the external data acquisition system. CDS works by taking an initial analog sample immediately after resetting the charge integrator. This sample also includes any residual signal from a previously selected multiplexed channel. Next, the multiplexed electrode transistor is turned on, and stored charge from the electrode and capacitor is measured in a second analog sample. An amplifier inside the acquisition IC amplifies the difference between these two analog samples and the resulting voltage is digitized. This process removes offset errors, crosstalk between multiplexer channels, and low frequency noise.

Using CS approaches in active electrodes also enables increased device reliability. Active electrode circuits for CS may be designed to operate entirely without a DC bias on the array by using multiplexer digital signals that are charge-balanced to have zero mean potential. This approach may increase the lifespan of the encapsulation used to protect the circuits on the array, enabling polymer-based approaches to last many years.

Alternative multiplexing strategy: Code-division multiple access (CDMA). Multiplexed arrays use TDM, in which transistors at each electrode switch between channels on the device to sample one electrode at a time. In some embodiments, other types of multiplexing may be used. For example, CDMA combines the transmitted signal with a pseudo-random code known to the transmitter and receiver; thus, multiple signals may be sent to a single receiver and separated using the pseudo-random code. CDMA is applied to an active electrode to directly multiplex the analog neural signal and test whether CDMA or other multiplexing strategies may reduce the aliased noise introduced by standard TDM.

Kriging. High-density spatial sampling is exploited to further reduce noise via optimal prediction using kriging techniques. The use of kriging—Gaussian process regression—is novel to electrophysiology and is particularly well-suited to estimate denoised potentials from high-resolution μECoG recordings. Kriging filters are adaptive to the spatial statistics of μECoG-recorded LFPs, such as correlation range, texture, and SNR. Reliance on spatial statistics gives kriging filters the desirable property of smoothing only as needed, and maintaining sharpness in high SNR and/or low correlation fields. Kriging prediction is optimally close to the underlying LFP in a mean square error sense, and explicitly estimates the amount of denoising error reduction, conditional on the statistical model.

High-density 3D sampling. The maximum recording distance between an extracellular electrode and a spiking neuron is ~150 μm. Therefore, 3D electrode arrays are needed that may interface with high-density neuronal circuitry in the mm-thick cerebral cortex at sub-150 μm distances. Known arrays such as micromachined tungsten or silicon microwire arrays have been established as mainstays for 3D neural probes, however, these arrays generally lack the ability to interface along the shanks and are essentially 2D. Known stacked Michigan-type neural probes or similar arrays are true 3D electrode arrays. However, besides being passive and having limited scalability, stacking is also against the interest of system miniaturization, and may be ineffective in terms of both cost and time. The Neuro-CROWN arrays separate themselves from existing neuro-electrodes in that they possess both high-resolution 3D interfacing capability and probe softness, and in that the final system is constructed from conventional 2D devices through a simple, deterministic rolling process.

Power density. The approach described herein minimizes power consumption and circuit complexity in the electrode array, and shifts the majority of the power consumption external to the brain. The goal is to produce multiplexed electrode arrays that record neural signals from thousands of channels with only a few external wire connections. While the approach may increase the complexity and power consumption of the external recording system, the trade-off is suitable for neural interfacing applications, because the recording system consumes power away from the brain, where power is not limited while increased power at the electrodes could cause damage to neurons.

Approach

Figure 16:
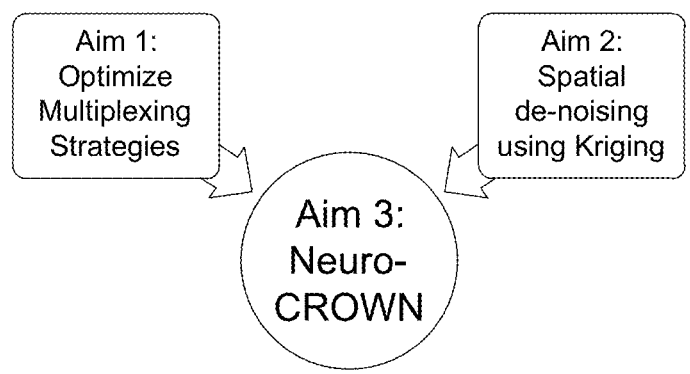
FIG. 16 provides a project flowchart. Optimized multiplexing strategies to reduce noise are developed in aim 1. In parallel, algorithms to reduce noise in spatially oversampled low field potentials (LFP) are refined in aim 2. The results of aims 1 and 2 are used in multiplexed Neuro-CROWN (CMOS-based, rollable, low-noise neuroelectronics) arrays in aim 3. The performance of the prototype Neuro-CROWN arrays are sufficient to be successfully manufactured and disseminated and may be further improved.

FIG. 16 shows the relationship among the aims. Electrode arrays with high resolution, high spatial coverage, and high SNR are developed. Multiplexing circuits and strategies are optimized (aim 1), data are spatially denoised through novel algorithms (such as Kriging, aim 2), and these techniques are implemented in a 3D, ultra-flexible, high-density, soft, penetrating electrode array to enhance the overall throughput and SNR of neural recordings (Neuro-CROWN, aim 3). The strategies described herein improve the performance of the Neuro-CROWN arrays.

Aim 1: Optimize circuit and multiplexing strategies to improve active array SNR.

Overview: Flexible active electrode arrays are improved by investigating CS rather than voltage-sensing electrode array designs. The data from circuit simulations, in vitro, and in vivo tests show that SNR in multiplexed arrays may be improved by utilizing CS circuit designs. A novel multiplexing strategy, CDMA, is tested. CDMA may reduce the amount of aliased noise in active electrode arrays. These improvements are tested using both in vitro and in vivo experiments. Finally, an optimized 4,096-channel multiplexed μECoG array is fabricated.

Figure 17A:
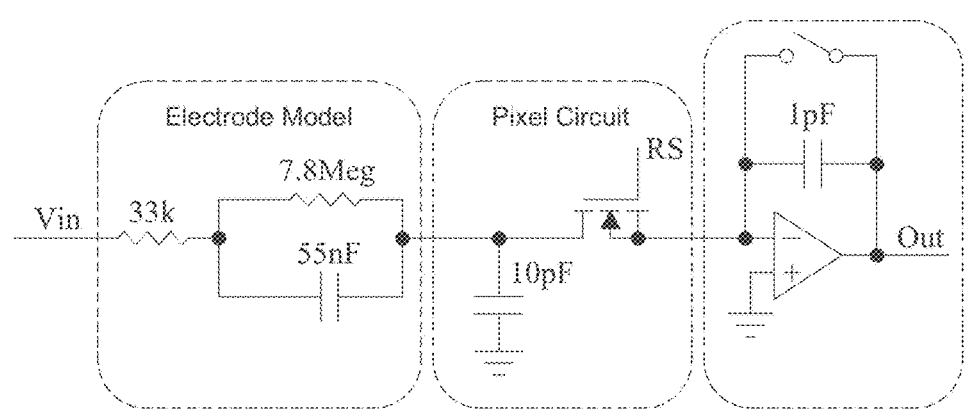
FIGS. 17A and 17B illustrate a SPICE (Simulation Program with Integrated Circuit Emphasis) circuit simulation. Circuit simulations of the CS 1T design using a 2mVpp sine wave at 500 Hz yielded an SNR of 70 dB and a noise level of 0.13 fC rms.
Figure 17B:
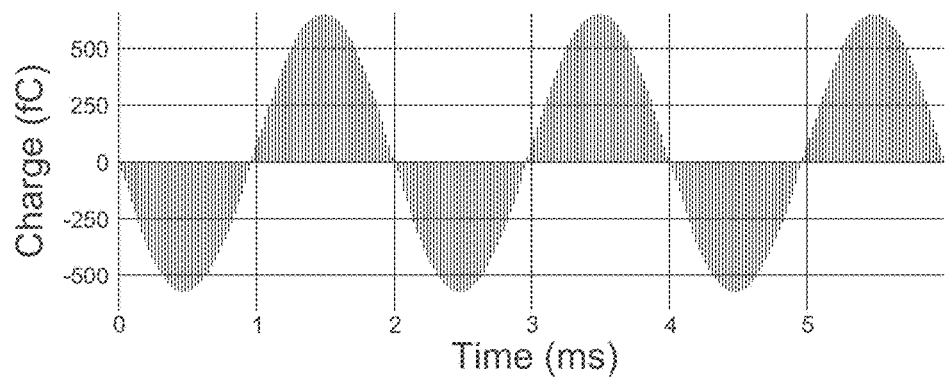

Data: Circuit simulations. Circuit simulations are performed using transistor models provided by a CMOS foundry. The 1T CS design (FIG. 15B) was simulated in a multiplexed array and an SNR of 70 dB was achieved using a 2 mVpp sine wave at 500 Hz and 57 dB using a 2 mVpp sine wave at 10 Hz (FIGS. 17A and 17B). The SNR was measured with two different sine wave frequencies since the electrode impedance is a function of frequency. The simulation included a Randles circuit model of a 40×40 μm2 Platinum-Iridium (PtIr) electrode. The 2 mVpp signal yielded 1.23 pC p-p at 500 Hz and 270 fC p-p at 10 Hz. The noise was 0.13 fC rms from 1-781 Hz.

The 1T CS design utilizes charge integration at each pixel to provide anti-aliasing, reducing noise and providing an advantage over voltage-sensing circuits (2T) at high multiplexing ratios. Noise from the 10 pF integration capacitor, multiplexing transistor, and the acquisition system was included. Noise from the electrode was excluded, as is standard for evaluating neural recording amplifier systems. This result exceeds the performance of Neuropixels.

Figure 18A:
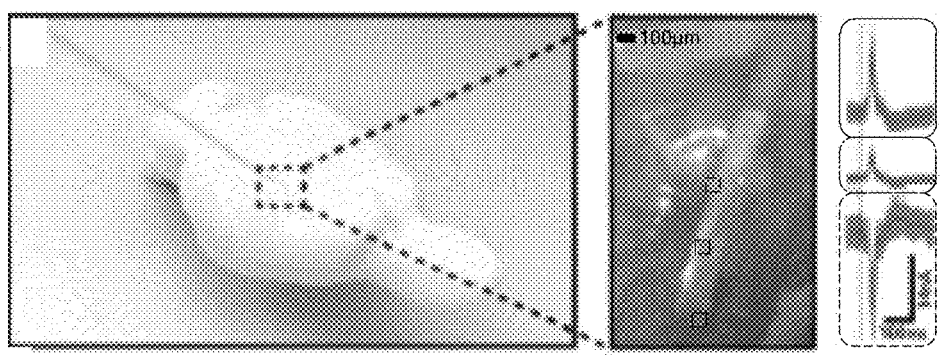
FIGS. 18A-18C show 1T multiplexed, current-sensing in vivo results.
Figure 18B:
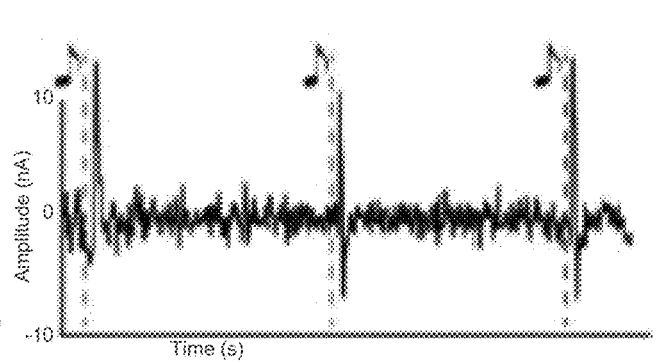

Data: In vitro. A flexible, multiplexed, 1T CS electrode array was fabricated and tested (FIGS. 18A-18C) (aim 3). The array had 256 Au/PEDOT:PSS electrodes, each 7×34 μm$^2$ with a center-to-center pitch of 30 μm, for a sensing area of 2 mm×0.36 mm. Neural currents were acquired using a custom multiplexed recording system, based on an ultra-low-noise CS amplifier. The CS amplifier measured electrode current rather than voltage, which is shown to have comparable or improved SNR in passive electrode recordings in vitro and in vivo. The CS amplifier integrated the current from 32 channels simultaneously. The CS amplifier also includes CDS and charge injection compensation, which reduces the effect of switching-induced transients during multiplexer switching. The outputs of the CS amplifier were measured using an 18-bit analog-to-digital (A2D) converter.

Experiments show that the 1T CS multiplexing design has lower noise than voltage-sensing multiplexed circuits. In vitro tests of the multiplexed 1T CS electrode recorded noise of 1.7±0.6 fC rms (1-390 Hz) and a SNR of 48±5.3 dB using a 2 mVpp, 10 Hz sine wave. The SNR includes noise from the electrode contacts and the recording system. The SNR is higher than Neuropixels (FIG. 14). The SNR and bandwidth may be further improved, based on the simulation results.

Figure 18C:
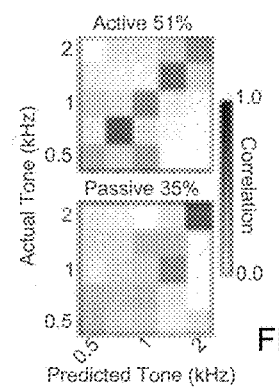

Data: In vivo. Multiplexed 1T CS electrodes (FIG. 18A) captured clear, single-trial auditory evoked responses (FIG. 18B) and decodable neural signals (FIG. 18C). Tone decoding accuracy was 51%, which was higher than passive electrode recordings from the same animal (35%). Tone decoding performance for a subset of tones (0.5-2 kHz) was focused on, because the array had high electrode density over a small area.

Task 1.1: Fabricate and optimize multiplexed, CS electrode with decreased aliased noise. A 64-ch multiplexed, CS active μECoG electrode is fabricated and tested and compared to a 61-ch passive (non-multiplexed) μECoG electrode. All the designs share the same geometry (8×8 array), resolution (400 μm pitch), and cortical coverage (~3×3 mm2). The performance of each electrode design is compared in in vitro and in vivo experiments. The sampling rate is increased to record spiking activity (~10 kHz) and validate improvements in SNR compared to traditional voltage sensing recordings.

In Vitro validation. The results of the simulation program are validated with Integrated Circuit Emphasis (SPICE) circuit simulations and the circuit designs are iteratively optimized. Input-referred noise, SNR, and crosstalk between electrodes are measured. The SNR at 2 mVpp and 10 Hz should be >40 dB. To measure crosstalk, a sine wave is input into one electrode while grounding the others and measure the amount of crosstalk into other multiplexed channels. Crosstalk should be less than −30 dB to independently sample the neural field.

In Vivo validation. In vivo recordings are performed using the 1T CS electrodes to measure the tone-evoked SNR (ESNR), spatial correlation, and tone-decoding accuracy. An acute subdural recording is completed over A1 auditory cortex in six anesthetized rats following established procedures. A range of 13 different tones (0.5-32 kHz, 0.5 octave spacing, 50 ms in duration, 2 ms cosine-squared) at 70 dB is played over a speaker inside the recording chamber while recording from the cortex. This allows for single trial tone decoding over a topological map of tone responses. The Klusta Python package is used to detect multiunit activity. In previous studies, the spatial autocorrelation of normally functioning arrays was an isotropic decreasing function of distance where arrays with correlation among columns, but not among rows, indicates one or more multiplexers with poor switching. ESNR should be equal to or greater than for recordings taken with a corresponding passive electrode (·8 dB). Spatial correlation should be isotropic (correlation values less than 0.1, based on previous unpublished results) showing that each multiplexed column is truly independent. Tone-decoding accuracy should be within 5% of the corresponding passive array performance.

Task 1.2: Investigate novel multiplexing strategies to reduce aliased noise. In this task, CDMA is applied to reduce aliased noise in an active electrode array. Instead of using the multiplexing transistor at each electrode as a switch, the multiplexing transistor is used as a mixer. The neural signals are modulated in the analog domain rather than converted from continuous time to discrete time. This prevents the introduction of aliased noise at the pixel. Anti-aliasing filters may be applied before A2D conversion of the multiplexed signals.

The analog neural signal is mixed with a pseudo-random code generated by the acquisition system. The output from multiple electrodes are combined together onto a single wire and then later deconvolved at the acquisition system. Each electrode that is multiplexed together uses a different pseudo-random code. For example, in a 32×32 array, all of the electrodes in a given row share the same pseudo-random code, and all of the electrodes in a given column share the same output wire. Thus, there are 32 mixed outputs that are deconvolved in software, reconstructing the original signals from all 1,024 electrodes.

CDMA is evaluated for neural electrodes in software simulations (Cadence and MATLAB). Input referred noise, SNR, and crosstalk between electrodes are measured. To measure noise, the input is grounded to the electrodes. The noise is characterized from 0 to 7.5 MHz, accounting for noise that is aliased from the maximum multiplexer rate, 15 MHz. The final device records LFP and single neuron activity; therefore, noise should be lower than 10 µV rms in both the LFP and spike bands. Hardware simulators are used to test CDMA in vitro and in vivo, as in task 1.1.

Figure 19A:
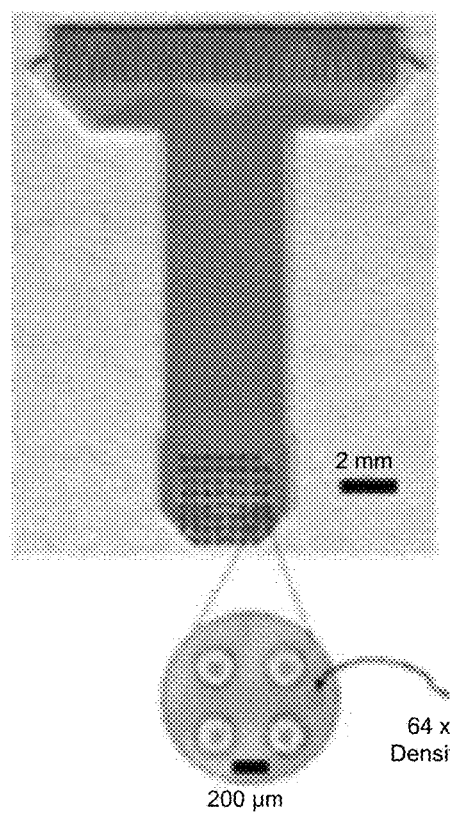
FIGS. 19A and 19B provide images and design of passive and active µECoG arrays.
Figure 19B:
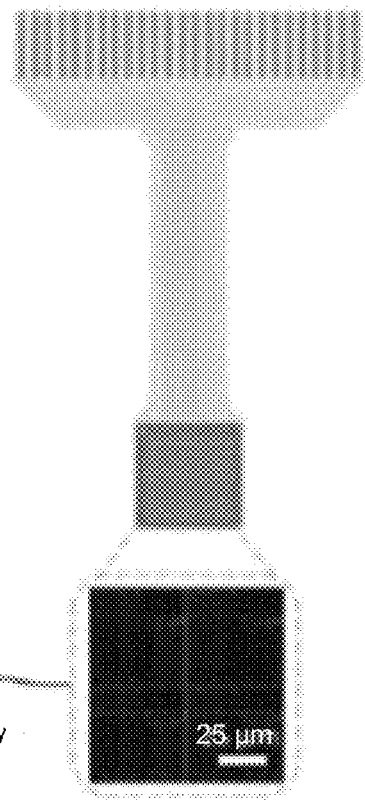

Task 1.3: Fabricate and disseminate an optimized 4,096-ch multiplexed µECoG array. In a separate effort, a 4,096-ch multiplexed µECoG array is fabricated using 2T voltage-sensing circuit design and TDM. This array has the same form factor as the passive and active arrays, but has 64× the resolution (50 µm pitch) (FIG. 19). The array is fabricated using commercial CMOS facility and is thinned using in-house post-fabrication techniques. While the circuits are optimized as much as possible to reduce noise, this array still has increased aliased noise compared to non-multiplexed arrays.

In this task, the optimized circuit and multiplexing strategies tested in tasks 1.1 and 1.2 are implemented to fabricate a second version of this electrode array with reduced noise. The array is fabricated as a monolithic or single-piece IC using the 0.6 µm silicon-on-insulator (SOI) process. A full wafer run of six wafers is ordered, yielding thousands of arrays at a cost of less than $5 per array. Thinning of the silicon dies is performed in house, using the oxide layer in the SOI wafer as a natural etch stop. The array is packaged in flexible liquid crystal polymer (LCP) cables and wired to an external data acquisition system. Once the device is fabricated, the device is evaluated in vitro and in vivo following the procedures outlined above. This noise-optimized 4,096-ch array is disseminated to the end-user group.

Aim 2: Spatially denoise neural signals using kriging.

Overview: Optimal linear prediction methods from geostatistics (kriging) is implemented to predict denoised local field potentials (LFPs) from noise-corrupted measurements. In general, linear smoothing filters applied to spatially over-sampled LFPs and uncorrelated noise result in noise reduction. Unlike kernel- or spline-smoothing, kriging filters are optimally adapted to the spatial statistics and SNR of LFPs. The degree of smoothing is conservative, because it depends on the spatial extent of correlated LFP and the amount of noise. Filters should be updated to adapt to time-varying field statistics. Model optimization is well-suited to fixed-rank matrix approximations and parallel GPU computation, making online processing feasible. Using these tools, the data stream is separated into spatially denoised LFPs and spiking activity.

Data: Geostatistics methodology is used to study spatial properties of cortical fields recorded by high density electrodes. Through analysis of spatial covariance models, it is found that potential fields in sensorimotor areas of neocortex are spatially correlated at all frequency bands up to at least 300 Hz. Correlated measurements may be used for optimal interpolation by forming linear predictors based on models of spatial covariance, a process known as kriging in geostatistics. The accuracy of spatial covariance models are assessed from a large dataset of 500 ms window µECoG by cross-validating predicted electrode potentials from training sets with actual recorded potentials from hold-out sets. The expected model-based error explained the cross-validation residual error with high accuracy in data from rat, monkey, and human ($r^2$>0.84).

Figures 20A, 20B:
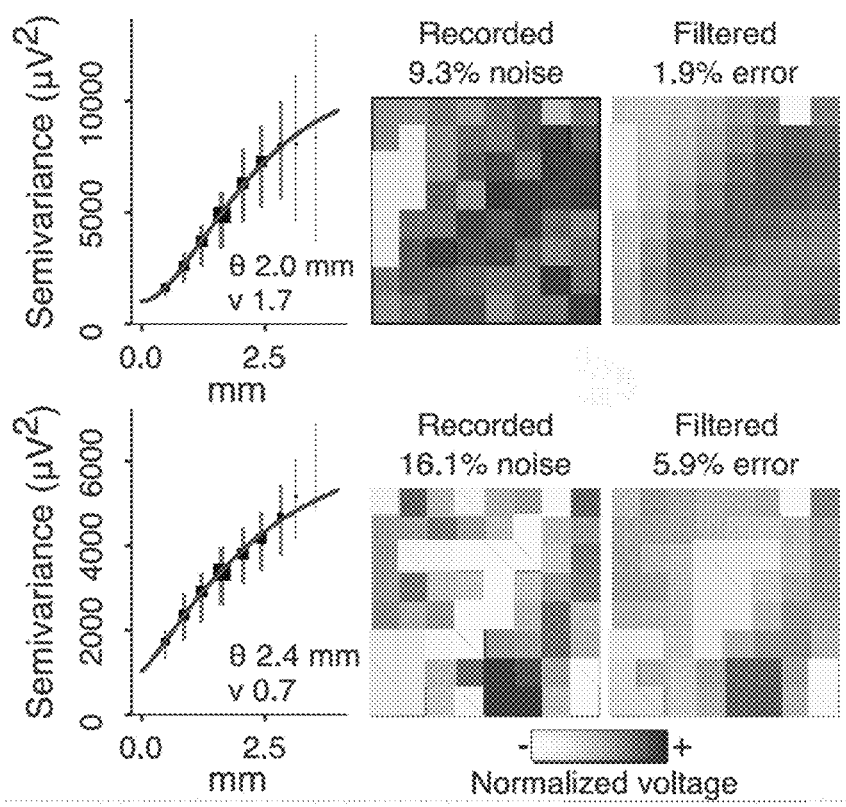
FIGS. 20A and 20B show kriging denoising based on spatial covariance models in a rat.
Figure 21A:
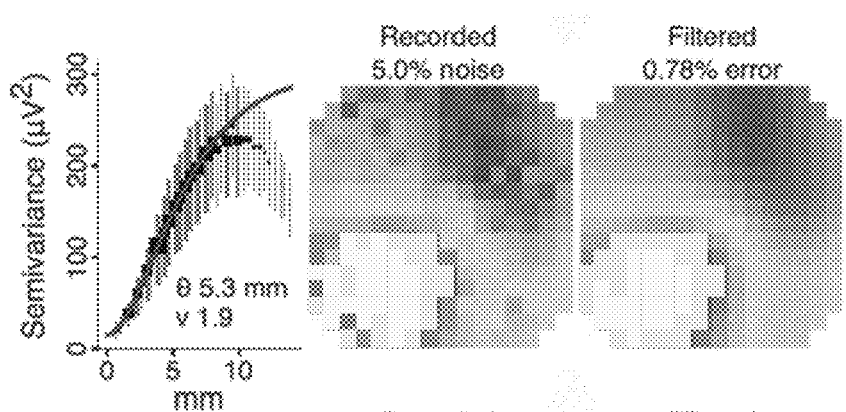
FIGS. 21A and 21B show a kriging denoising in human motor cortex. Different filter efficiency was seen based on the spatial statistics in FIGS. 21A and 21B.
Figure 21B:
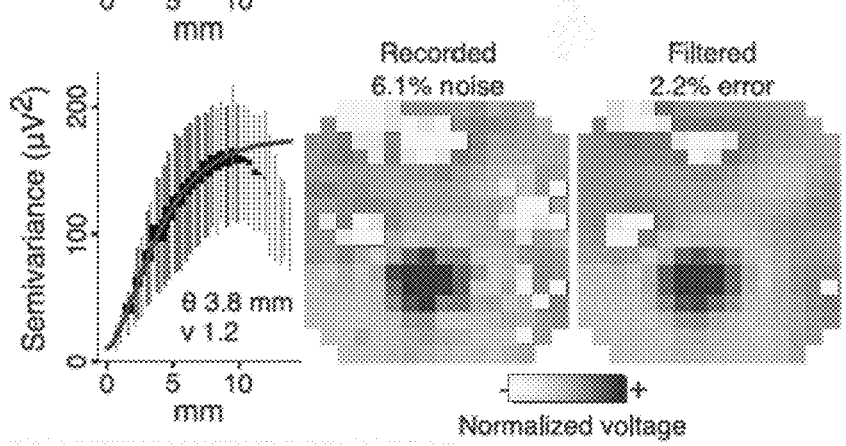
Figure 22A:
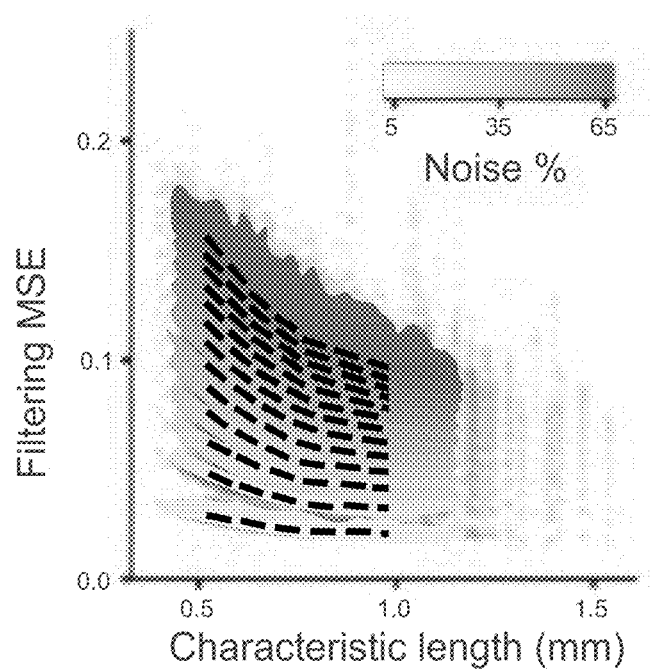
FIGS. 22A and 22B show denoising efficiency for low-noise µECoG fields with simulated additive noise.
Figure 22B:
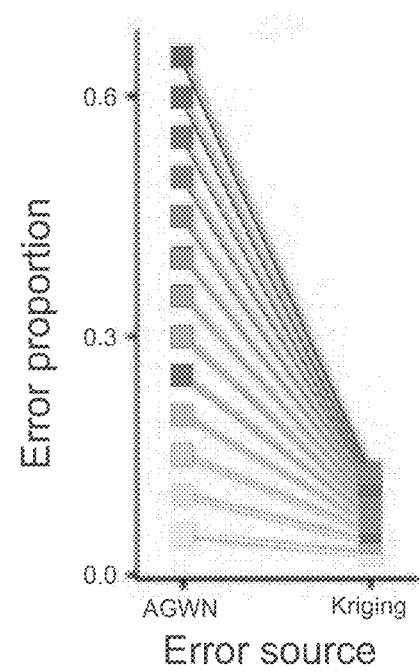

Predicting denoised potentials at the original electrode sites may be applied. FIGS. 20A and 20B show optimally filtered frames from an actively multiplexed electrode recording of rat auditory cortex. Results from human motor cortex are shown in FIGS. 21A and 21B. The filter weights and noise reduction in each case were optimized based on the spatial statistics for a short-time window. The covariance models were cross-validated as described above, but the stated filter errors were conditional on the model of the unobservable "true" neural fields. To confirm the model-based denoising efficiency, electrode recordings with 0.5% median noise were used to approximate true neural fields, and simulated additive Gaussian white noise (AGWN) in different proportions. Each 500 ms window had a unique kriging filter and expected value for error, based on spatial statistics (including additive noise). Filtering accuracy improved with larger characteristic correlation lengths, and noise reduction increased in higher additive noise (FIGS. 22A and 22B). The expected error predicted the real filtering error (linear regression slope=1.04, $r^2$=0.993), which validated the denoising estimates reported by the kriging method.

Task 2.1: Refine covariance modeling for continuous adaptation to denoise µECoG recordings offline. The knowledge derived from the study of µECoG spatial field characteristics is built on to produce a denoising algorithm that continually adapts to spatiotemporal dynamics. Stability is emphasized to promote automation and computational efficiency, to provide a scalable path to large channel electrode grids including the 2,048-ch Neuro-CROWN array and 4096-ch CMOS µECoG array.

The optimization of spatial covariance models is refactored to use more robust likelihood maximization. This method of parameter optimization balances data fitting with a penalty for model complexity. Maximum-likelihood of leave-one-out predictions is also explored, which has a similar computational burden. The stability of both methods is greatly improved with a strong prior estimate of noise in the µECoG recording. Measurement noise is accurately estimated using a singular value thresholding heuristic, or the model noise value may be based on in vitro noise characterization in saline.

Model optimization and filtering are updated based on latent state switching. The total signal power of a short window of µECoG modulates the SNR, which is an important parameter affecting integration radius in kriging filters. It has been observed that power is a predictor of the characteristic length of the covariance model. A time series of latent states are determined using a Hidden Markov Model (HMM) of the average power envelope of signal segments. A new spatial model is estimated for each sustained state transition in the series.

Figure 23:
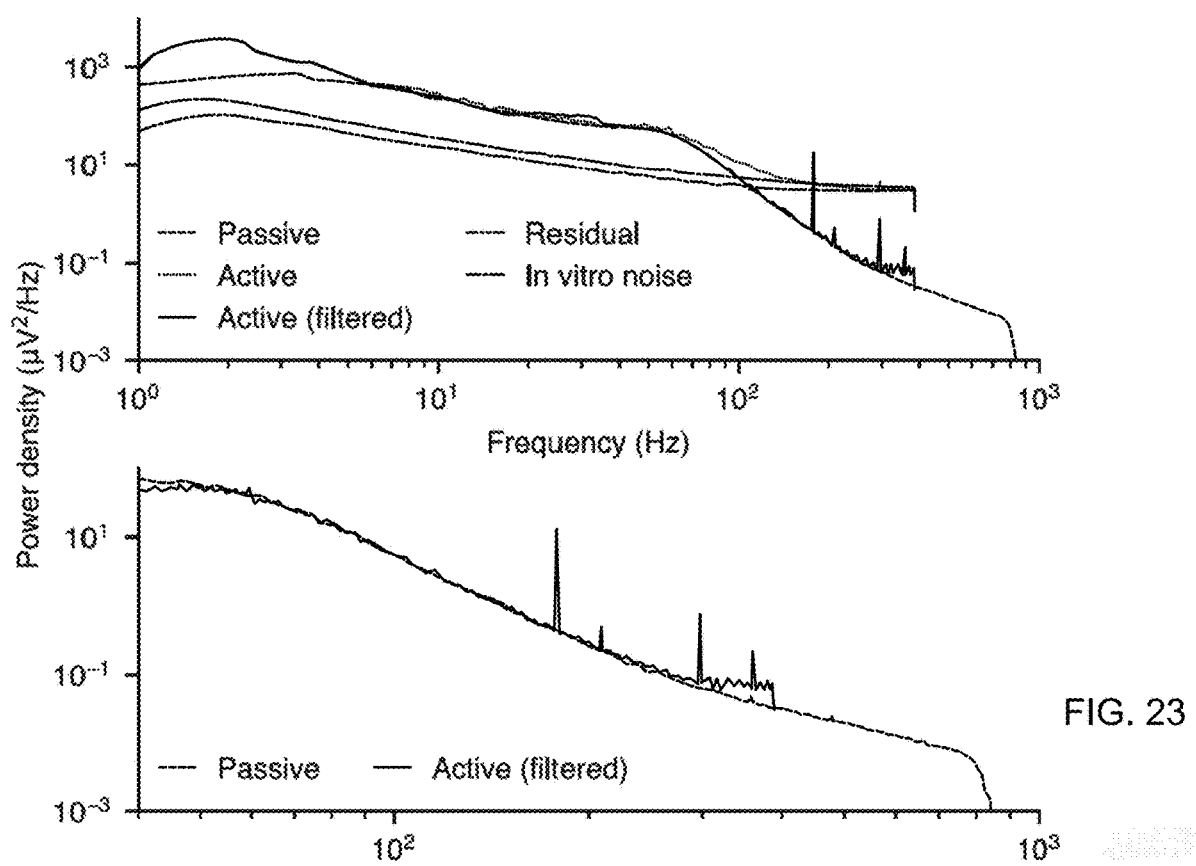
FIG. 23 illustrates power spectral densities of denoised µECoG signals. The instrumentation noise of the active array intersected the neural signal power at ~100 Hz. After denoising, the PSD closely matches the power levels measured with a low noise passive array.
Figure 24A:
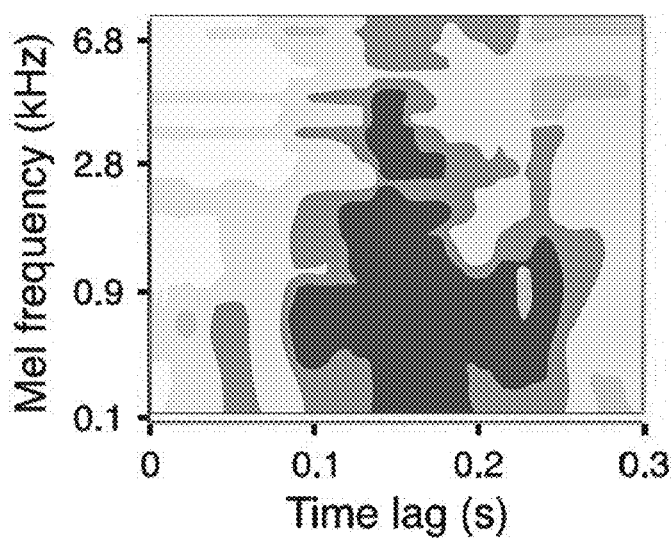
FIGS. 24A and 24B illustrate that filtering improves spectro-temporal receptive field (STRF) modeling.
Figure 24B:
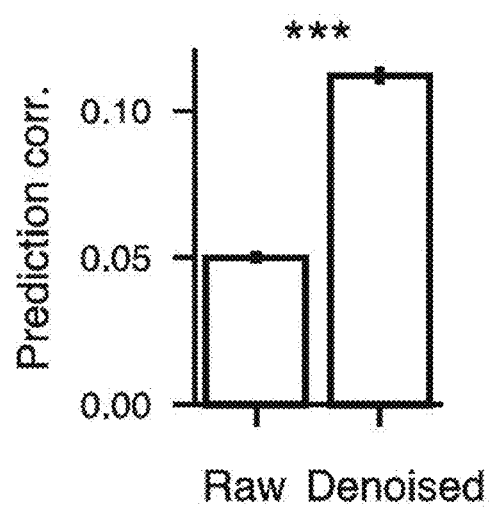

The spatial statistics of LFP vary with temporal bandpass. The discrete wavelet transform is used to denoise µECoG frames with frequency-resolved models. A single wavelet subband is a time series that preserves the spatial correlation at the corresponding frequency band. The preceding estimation and filtering stages may be applied in parallel for multiple wavelet decomposition levels and assemble the coefficients to construct denoised recordings across the full LFP bandwidth. Testing of this algorithm has indicated an accurate separation of signal and noise power. FIG. 23 shows power spectral densities (PSDs) of noisy "active" recordings and virtually noiseless "passive" recordings made sequentially in rat auditory cortex. The PSD of the denoised signal largely overlaps the low-noise passive PSD, including at frequencies above the intersection with the noise floor. In this example, the heuristically derived noise floor (i.e. the residual PSD) is a close but conservative estimate of the noise that was measured in vitro. Denoising also improved the prediction of high gamma (75-150 Hz) power in human superior temporal gyms based on spectro-temporal receptive field models of neural responses to human speech (FIGS. 24A and 24B).

To refine the methods, multiple existing datasets from rat, monkey, and human, recorded with different electrode geometries are used. During initial development, previously developed µECoG validation metrics are used to evaluate improvement in sensitivity to event-related activity. In subsequent stages, end-users are engaged with to assess improvements in speech and kinematics decoding in human and monkey, respectively. Existing Neuropixels array recordings are also used to investigate learning spatial filters to improve sensitivity to neural activity in the spike band.

Task 2.2: Scale kriging filter optimization to enable online denoising of large channel arrays. The computation time to denoise 100×1 second blocks of 64-channel µECoG sampled at 781 S/s was 267 seconds, using implementation of adaptive spatial denoising. The matrix inversion of the spatial covariance kernel, which is a central component to model optimization, has O(N3) computational cost for N electrodes. That cost scaling presents a challenge for a naïve implementation for the proposed counts of up to 4096 electrodes. The computation of spatial filtering is simplified by using covariance kernel simplifications with optimization and linear algebra implemented in graphical processing units (GPUs).

Two approaches are investigated to reduce matrix operations. A simplification to the covariance matrix may be made for data on a regular grid when covariance kernel functions are separable as products across the two spatial axes of the grid. For the 4096-ch array with a 64×64 grid, the corresponding covariance matrix may be expressed as a Kronecker product of two 64×64 matrices. Algebraic identities of the product reduce matrix inversion complexity from polynomial O(N3) to linear O(N) cost.

A second simplification may be made by reducing the rank of the covariance matrix. Fixed-rank kriging assumes that the N-dimensional random LFP process is a linear expansion of a smaller R-dimensional process that may adequately explain LFP spatial variation. The Sherman-Morrison-Woodbury identity reduces the inverting matrix to R x R, making kriging complexity O(N) when R is small. Fixed-rank kriging performed favorably in computation time and prediction accuracy among a large set of algorithms for largescale spatial prediction 61.

Aside from algebraic simplifications, GPUs are used to accelerate computation. GPU architecture favors parallelized computation, but model optimization and matrix decompositions are inherently iterative procedures. By reducing the complexity of each optimization problem using Kronecker product identities and/or fixed-rank kriging, several models may be optimized in parallel. A software toolkit, Gpufit, was designed to determine the best use of GPU resources for multiple separate optimization problems. To enable low-latency denoising, the methods for online HMM state estimation for wavelet subbands computed over moving windows are used.

Scalability is initially assessed using existing recordings from a 1008-channel grid. To deploy the spatial denoising algorithm to the end-users, this algorithm is packaged with a high-level computing language (Python). Using Python, GPU-aware computational libraries (e.g. TensorFlow) may be interfaced with and subroutines in the C language may be optimized as needed to achieve online performance for large channel counts. Scaling to large arrays with high sampling rates may be challenging. If online performance cannot be achieved, the denoising algorithm is still deployable as an offline tool. Additional heuristics and simplifications are investigated to reduce computational complexity.

Aim 3: Develop and validate an ultra-flexible, high-density, low-noise 3D active microelectrode array.

Overview. In this aim, rolling of 2D soft electrode array (ROSE) method from passive arrays is migrated to optimized low-noise, active arrays with 2,048 simultaneously measured channels distributed in 3D. The 2,048-ch CMOS-based, rollable, low-noise neuroelectronic (Neuro-CROWN) arrays include faradaic electrodes as small as 10×18 µm$^2$, and a microelectrode density of over 1,152/mm$^3$. Ultra-thin (down to 10 µm) polymer shanks are used for reduced insertion footprint and optimize their in vivo insertion in rodents. Optimization of the rolled configuration, substrate/encapsulation materials, thicknesses, shank profile, and temporary stiffening for insertion using in vitro characterization, chronic (3-month) in vivo tissue biocompatibility assessments, and recording evaluation from the rodent brain are performed.

Data: The ROSE method is used to enable the formation of monolithic, 3D, soft electrode arrays from conventional 2D devices. The process started with a fully formed 2D shank array on flexible Kapton (total device thickness ~30 µm). A soft PDMS layer (100-400 µm thick) was then bonded on the base region of the array to serve as the spacer between the eventual rolling laps (FIG. 25A). A method of rolling includes bonding an ultra-small-diameter (~250 µm) stainless steel mandrel on one of the short edges of the base region, and rotating the mandrel towards the PDMS to roll the device into a 3D shape (FIG. 25B). The final shape may be secured in different ways, such as by using a thin-film, medical adhesive tape. The prototype 256-ch 3D ROSE array had 64 shanks with a 200 µm inter-shank pitch (FIG. 25B), each with four Au/PEDOT:PSS electrodes that were 10×20 µm2 with a pitch of 100 µm. With a 200 µm PDMS spacer, the electrode density in the 3D array was ~576/mm3. Each shank had a length of 1.5 mm, width of 110 µm, thickness of 30 µm, and a tapered profile with a tip angle of 37° to facilitate insertion and to minimize tissue damage. Since the rolling process is non-destructive, 3D arrays achieved from this ROSE method have demonstrated uniformly low impedance (average ~268 kΩ at 1 kHz) and high yield (FIG. 25C). The strain of the electrodes in the shanks is negligible (FIG. 25D) due to the shanks' narrow and long nature, which mechanically isolates the electrode region from the rolling. In the rolled base, the strain is also small (<3% compressive), and does not affect the metal interconnects; this strain may be further reduced by moving interconnect layers to the neutral mechanical plane in the base. The shank positions in the final 3D configuration are highly deterministic (FIG. 25E) from the design of the initial 2D array, diameter of the mandrel, and thickness of the PDMS spacer. The complete freedom in the 2D design allows for customized shank numbers, shank geometries, and electrode densities and locations.

Figure 25F:
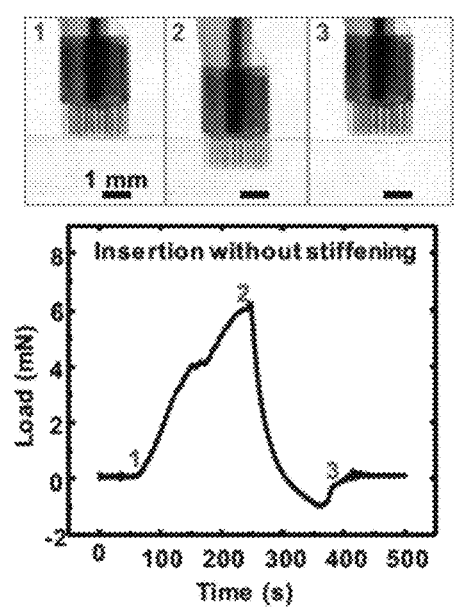
Figure 25G:
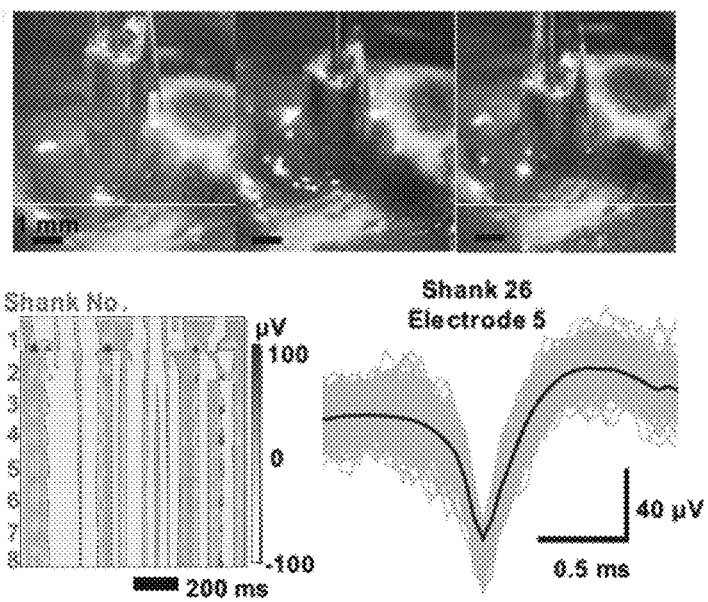

The insertion dynamics of the 3D ROSE array is characterized and the array is validated in vivo. All 64 flexible shanks were successfully inserted into the agarose gel brain phantom without buckling at an insertion speed of 500 µm/min (FIG. 25F). The maximum force of the insertion, which depends on the shank tip angles, dimensions, insertion speed, and total shank number was 6.2 mN when the shanks were fully inserted. Implantation in rat cortex validated the 64-shank 3D ROSE array, with successful recording of both LFPs and spikes (FIG. 25G).

Task 3.1: Formation of 2,048-ch Neuro-CROWN array with ultra-thin chiplets of optimized CMOS electrodes. The electrodes and multiplexer circuits in the Neuro-CROWN array is fabricated using 0.6-micron SOI CMOS Technology. A 32:1 multiplexed electrode array chiplet is designed with 32 electrodes arranged in one column (10×18 µm2 electrodes, 50-µm pitch). One chiplet is integrated into each of the 64 shanks of the Neuro-CROWN. The 32 electrodes require only 6 external wire connections, of which 5 are shared among all 64 shanks, resulting in a total of only 69 wires for the 2,048 electrodes. Interdigital arrays of 64 repetitions maximize the utilization of the wafer dies to reduce cost to ~$10 per array. A CMOS-compatible low-impedance coating such as TiN is used to reduce the microelectrode impedance (<200 kΩ). Long-term durable thermal-oxide encapsulation is used through the hermetic via design.

Figure 26A:
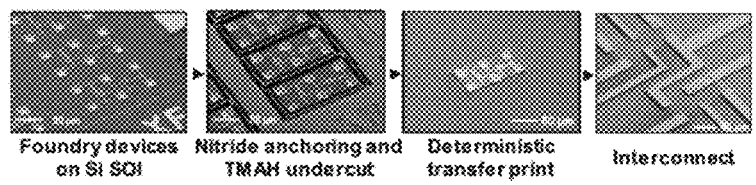
FIGS. 26A-26C shows Neuro-CROWN fabrication and insertion.
Figure 26B:
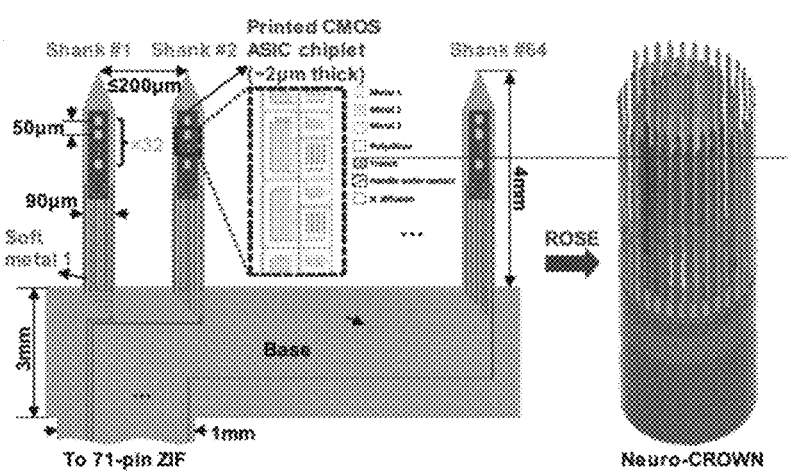
Figure 26C:
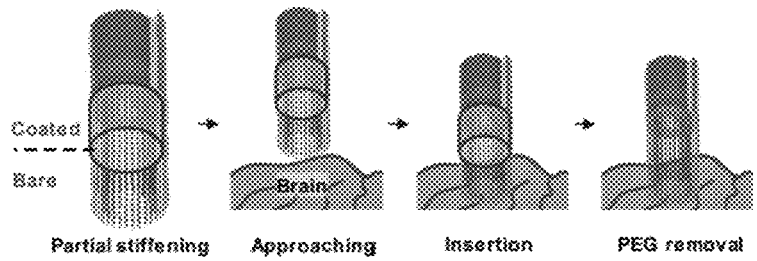

An advanced post-processing is used to transfer-print the ultra-thin (~2 µm) CMOS electrode chiplets from the bulk SOI wafer fabricated at a facility to serve as the soft CMOS neuroelectrodes in Neuro-CROWN. This transfer processing is developed and validated, which successfully printed and interconnected foundry-fabricated 2.1 µm-thick CMOS chiplets (FIG. 26A), with 100% yield involving ~1,000 micro-chiplets over an area up to 1.5×1.5 cm2. Here, 64 chiplets are transfer-printed to the shank regions of the flexible 2D precursor substrate (1-15 µm thick) of Neuro-CROWN all at once (FIG. 26B). Both polyimide and parylene C are leveraged. Both substrates are suitable for soft penetrating arrays. After foundry fabrication, a low-stress SiNx layer (600 nm thick) is deposited and patterned on the wafer to serve as the etching barrier material of active devices, and as anchors so as to tether the SOI device blocks to their lithographically defined locations and to prevent them from floating away during the undercut etching process. This etching involves complete immersion of devices in a static base solution at 85° C. Devices released in this way exist in a freely suspended configuration, suitable for transfer-printing from the source wafer onto the target substrate. The transfer stamp is made from glass and elastomer by a simple inexpensive injection-molding technique. Custom relief structures on the stamp surface pick up the released device layer selectively from the SOI substrate, then print them onto the electrode region of the substrate, where the ultra-thin, flexible form factor (down to a few microns in thickness) is leveraged, which has demonstrated chronic reliability and biocompatibility. A coating of a low-modulus polyimide (~1 µm thick) served as an adhesive to achieve 100% transfer. After this polyimide-device stack has been cured, the device layer is permanently fixed. After removing the SiNx anchor layer, a top-coat of polyimide (~2 µm thick) is spun over the CMOS chiplets, embedding and planarizing them for the subsequent interconnections. FIG. 26A shows the transferred devices are interconnected on thin flexible substrates. The simple two-layer gold interconnects are formed using standard metallization and eventually fan out to high-density zero insertion-force pads, which serve as the interface to the acquisition system (FIG. 26B). Ultra-thin (≤1 µm) encapsulation on the shank region is achieved by leveraging advanced multilayer technology, in addition to the existing thermal oxide. To form the electrode shanks, nickel (300 nm thick) and photoresist S1818 (10 µm thick) serve as the hard mask for ICP-RIE etching. The ROSE method is then applied to the 2D array to form the 3D Neuro-CROWN array, ready for bench testing. The CMOS chiplets are not strained due to the narrow nature of the shanks (see FIG. 25D).

A minimized insertion footprint may significantly diminish penetration trauma and subsequent inflammatory response. To this end, the shank profile (width, thickness, and tip angle) and insertion strategy are optimized. The partial stiffening technique (FIG. 26C) is leveraged to insert the electrodes without increasing the insertion footprint. This technique takes advantage of bending mechanics: the buckling force threshold of a thin beam is inversely proportional to the square of its length, which is why the 256-ch 3D ROSE array was successfully implanted without aiding insertion (FIG. 25F). The close-to-base portion of the shanks is partially stiffened by using biodegradable polymers such as polyethylene glycol (PEG), to temporarily reduce the shank length to provide a buckling force over 10 mN, sufficient to penetrate the brain. The embedded CMOS chiplet in the shank also works in favor of insertion due to the higher modulus from the inorganic device layer. After all shanks are inserted to the desired depth, the biodegradable polymer brace is incrementally dissolved in saline. Using brain phantoms such as polyvinyl chloride (PVC), the force dynamics of shank insertion and retraction are carefully evaluated, and electrode damage is assessed. For ultra-thin shanks, incremental dissolution is performed to allow only a short length of bare shanks to be exposed then inserted.

Task 3.2: Validation of Neuro-CROWN chronically in vivo. For long-term recording/compatibility assessment, the best three configurations of the Neuro-CROWN arrays from bench testing are directly compared to silicon-based arrays purchased from NeuroNexus, contralaterally implanted. Specifically, 15 wild type (WT) rats (Jackson Laboratories) per configuration are anesthetized. Prior to long-term implantation, the Neuro-CROWN arrays are sterilized with ethylene oxide. Both a stiff NeuroNexus and the Neuro-CROWN devices are symmetrically implanted into primary auditory cortex of each rat and cemented to the skull.

To assess the long-term functionality of the Neuro-CROWN, weekly electrophysiological recordings are performed from the implanted rats during free behavior in a sound-attenuated enclosure. Auditory evoked responses are record. Both local field potential (LFP) and spike level (filter settings for LFPs: 1-1000 Hz, f=3 kHz; spikes: 0.3-8 kHz, f=30 kHz) are recorded while video-monitoring rat trajectories to account for possible movement artifacts. Data are analyzed offline using algorithms to assess spectral composition of the LFP and a threshold-based detection of spikes using wavelet decomposition followed by superparamagnetic clustering. Cluster quality is quantified by L-ratio and isolation distance measures. The first recording session immediately follows the recovery of the implanted rats from the general anesthesia. To evaluate the SNR for both soft and firm microelectrode arrays devices, the noise is calculated as root-mean-square (RMS) amplitude during interspike intervals (ISI). The signal is calculated as RMS for the detected spikes, concatenated to one trace. Although the Neuro CROWN electrodes is expected to maintain high SNR over the course of the proposed three months, a SNR decrease over time may occur. Differences between microelectrode arrays and the quality of their recordings are evaluated by quantifying the number of single units and SNR. Multivariate methods are employed depending on their distributions (e.g. two-way MANOVA or Friedman test in the multivariate extension, followed by post hoc analysis).

Terminal tissue evaluation is performed at 2, 8, and 16 weeks. Following the last recording, 5 rats per group are transcardially perfused and fixed with 4% paraformaldehyde in PBS. The implants are removed from the isolated rat brains and preserve them for further SEM analysis. The fixed and encapsulated (5% agarose) brains are sectioned using a vibratome (50 μm thickness). Three series of tissue slice examination are used to investigate tissue-device biocompatibility. Images of the area surrounding the symmetrically implanted microelectrode arrays are collected with the identical settings. Z-stacks are reconstructed and fluorescence is quantified at the implantation site for the flexible array and compared to the same area in the contralateral, silicon-implanted hemisphere. Co-staining is performed, such as for the neuronal marker NeuN (rabbit polyclonal, anti-FOX3/NeuN antibody, Abcam), the neural degeneration marker Fluoro-Jade C (FJC, Millipore), the astrocyte marker GFAP (chicken polyclonal, anti-GFAP antibody, Abcam) and the nuclear stain DAPI to assess the number of remaining neurons around the implantation site, to quantify acutely degenerating neurons, to evaluate astrocyte reactivity, and to evaluate microglial activity and their phagocytosis around the implants.

At least one technical effect of the systems and methods described herein includes (a) a brain computer interface having active electrodes via multiplexing; (b) a brain computer interfaces having an increased SNR via a front-end circuit at the site of each electrode; (c) optimizing the circuit design for the brain computer interface to be suitable for being inserted on the brain; (d) proving a flexible circuit having a relatively small thickness in the brain computer interface by transfer-printing; (e) reducing noise in the signals by kriging filtering; and (f) method of fabricating a 3D brain computer interface by rolling.

Example embodiments of systems and methods of systems and methods for brain computer interfaces are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A brain computer interface for interfacing with a brain of a subject, the brain computer interface comprising:
   one or more shanks, wherein each shank comprises:
      an array of pixels, wherein each pixel comprises:
         an electrode; and
         a front-end circuit positioned at a site of the electrode, the front-end circuit configured to reduce noise in signals recorded by the electrode, and the front-end circuit further configured to multiplex the signals,
         wherein a density of power consumption of the each pixel is equal to or less than 1 μW per area of 50 μm by 50 μm; and
      output traces electrically coupled with the array of pixels, wherein a number of output traces is less than a number of pixels in the array due to multiplexing,
   wherein the one or more shanks are configured to be inserted on and/or into a brain of a subject.

2. The brain computer interface of claim 1, wherein the brain computer interface is scalable in a range direction and/or a depth direction.

3. The brain computer interface of claim 1, wherein the front-end circuit comprises a low pass filter configured to reduce aliased noise.

4. The brain computer interface of claim 3, wherein a resistor of the low pass filter comprises an output resistance from an upstream circuit of the low pass filter.

5. The brain computer interface of claim 1, wherein the front-end circuit comprises a high pass filter, the high pass filter comprising a resistor and a capacitor, and a capacitance of the capacitor is selected to reduce flicker noise and/or thermal noise in the front-end circuit.

6. The brain computer interface of claim 5, wherein the resistor is selected to have a relatively large resistance such that the high pass filter has a relatively low cutoff frequency.

7. The brain computer interface of claim 6, wherein the front-end circuit further comprises a circuitry configured to tune a resistance of the resistor.

8. The brain computer interface of claim 1, wherein signals output from the brain computer interface have a frequency range including a frequency range corresponding to local field potentials and a frequency range corresponding to action potentials.

9. The brain computer interface of claim 1, wherein the front-end circuit comprises a multiplexer configured to multiplex the signals from the electrode.

10. The brain computer interface of claim 9, wherein the multiplexer is integrated with correlated double sampling circuitry configured to reduce noise in sampled signals.

11. The brain computer interface of claim 1, wherein the front-end circuit comprises a multiplexer configured to multiplex the signals from the electrode via a code-division multiple access (CDMA) scheme.

12. A method of fabricating a brain computer interface for interfacing with a brain of a subject, comprising:
   forming one or more shanks, wherein each shank includes:
      an array of pixels, wherein each pixel includes:
         an electrode; and
         a front-end circuit at a site of the electrode, the front-end circuit is configured to reduce noise in signals recorded by the electrode, and the front-end circuit further configured to multiplex the signals,
      wherein a density of power consumption of the each pixel is equal to or less than 1 μW per area of 50 μm by 50 μm; and
      output traces electrically coupled with the array of pixels, wherein a number of output traces is less than a number of pixels in the array due to multiplexing,
      wherein the one or more shanks are configured to be inserted on and/or into a brain of a subject; and
   transferring the one or more shanks to a substrate.

13. The method of claim 12, wherein:
   forming the one or more shanks further comprises forming the one or more shanks in a die; and
   transferring the one or more shanks further comprises providing a barrier to prevent mechanical cracks from travelling to a shank during the transferring by:
      coupling a seal ring around the shank.

14. The method of claim 12, wherein transferring the one or more shanks further comprises:
   transfer-printing the one or more shanks.

15. The method of claim 12 further comprising:
   optimizing a circuit design of the front-end circuit by:
      limiting circuit parameters to meet predetermined thresholds.

16. The method of claim 15, wherein the circuit parameters comprises power consumption at an area, input referred noise, and/or bandwidths of filters.

17. The method of claim 12 further comprising:
   bonding an elastomeric layer with an array of shanks; and
   rolling the array of shanks into a three-dimensional (3D) shape.

18. The method of claim 12 further comprising:
   partially stiffening the one or more shanks by:
      bonding the one or more shanks with a biodegradable layer positioned approximate an insertion end of the one or more shanks.

19. The method of claim 12, wherein forming the one or more shanks further comprises:
   forming the one or more shanks, wherein at least one of the one or more shanks comprises a tapered tip configured to facilitate insertion of the one or more shanks into the brain.

20. A brain computer interface system comprising:
   a brain computer interface configured to interface with neurons of a brain of a subject, the brain computer interface comprising:
      one or more shanks, wherein each shank comprises:
         an array of pixels, wherein each pixel comprises:
            an electrode; and
            a front-end circuit positioned at a site of the electrode, the front-end circuit configured to reduce noise in signals recorded by the electrode, and the front-end circuit further configured to multiplex the signals,
         wherein a density of power consumption of the each pixel is equal to or less than 1 μW per area of 50 μm by 50 μm; and
         output traces electrically coupled with the array of pixels, wherein a number of output traces is less than a number of pixels in the array due to multiplexing,
         wherein the one or more shanks are configured to be inserted on and/or into a brain of a subject; and
   a brain computer interface (BCI) computing device electrically coupled with the brain computer interface, the BCI computing device comprising at least one processor in communication with at least one memory device, and the at least one processor programmed to process signals output by the brain computer interface.

21. The brain computer interface system of claim 20, wherein the at least one processor is further programmed to:
   reduce noise in signals corresponding to local field potentials by:
      applying kriging filters to the signals output by the brain computer interface.

* * * * *